(12) United States Patent
Shaber et al.

(10) Patent No.: US 7,473,669 B2
(45) Date of Patent: *Jan. 6, 2009

(54) SUBSTITUTED 4,5-DIHYDRO-1,2,4-TRIAZIN-6-ONES, 1,2,4-TRIAZIN-6-ONES, AND THEIR USE AS FUNGICIDES

(75) Inventors: Steven Howard Shaber, Zionsville, IN (US); Maurice Chee Hoong Yap, Zionsville, IN (US); Kevin Gerald Meyer, Zionsville, IN (US); Noormohamed Mohamed Niyaz, Indianapolis, IN (US); Brent Jeffrey Rieder, Greenfield, IN (US); Michael Thomas Sullenberger, Westfield, IN (US); William Randal Erickson, Carmel, IN (US); Frisby Davis Smith, Pittsboro, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/417,327

(22) Filed: May 3, 2006

(65) Prior Publication Data

US 2006/0252755 A1 Nov. 9, 2006

Related U.S. Application Data

(60) Provisional application No. 60/677,434, filed on May 3, 2005.

(51) Int. Cl.
*C07D 253/06* (2006.01)
*C07D 253/065* (2006.01)
*C07D 253/10* (2006.01)
*A01N 43/707* (2006.01)
*A61K 31/53* (2006.01)

(52) U.S. Cl. .................. 504/228; 504/229; 504/230; 544/182; 544/183; 544/184

(58) Field of Classification Search .......... 544/182, 544/183, 184; 504/228, 229, 230
See application file for complete search history.

(56) References Cited

U.S. PATENT DOCUMENTS

| 4,716,164 A | * | 12/1987 | Hargreaves et al. | ......... 514/243 |
| 5,574,033 A | * | 11/1996 | Kobayashi et al. | ....... 514/222.5 |
| 6,159,980 A | * | 12/2000 | Arvanitis et al. | ....... 514/252.02 |
| 6,825,192 B1 | | 11/2004 | Ito et al. | |

FOREIGN PATENT DOCUMENTS

| DE | 42 39 542 A1 | 5/1994 |
| WO | WO-00/47567 A1 * | 8/2000 |
| WO | WO 01/00598 | 1/2001 |
| WO | WO 02/067675 | 9/2002 |

OTHER PUBLICATIONS

Laurent Sanière, et al, Novel Approaches to Optically Active Substituted 4,5-Dihydro-1,2,4-Trianzin-6(1H)-Ones as Conformationally Constrained Peptidomimetics, Heterocycles, vol. 55, No. 4, 2001, pp. 671-688.
David J. Collins, et al, Dihydro-1,2,4-Triazin-6(1H)-Ones. IV, Aust. J.Chem, 2000, 53, 137-141.
Ahmad S. Abushamleh, et al, Synthesis and Structural Characterization of Palladium(II) Complex with (L)-3-Acetyl-5-Benzyl-1-Phenyl-4,5-Dihydro-1,2,4-Triazin-6-One Oxime. Part II, Hetrocycles, vol. 53, No. 8, pp. 1737-1744.
Ahmad S. Abushamleh, et al, Transition Metal Complexes of Drivatized Chiral Dihydro-1,2,4-Triazin-6-Ones. Part I. Nickel (II) Complex of (D)-3-Acetyl-5-Benzyl-1-Phenyl-4,5-Dihydro-1,2,4-Triazin-6-One Oxime. An Instance of A Carbon-Carbon Coupling Reaction. Heterocycles, vol. 53, No. 5, 2000, pp. 1155-1165.I.
Adel M. Awadallah, et al, Cyclocondensation Reactions Of Nitrilimines: Synthesis o 1,2,4-Triazin-6-Ones and 1,2,4,5-Tetrazines. Hetrocyclic Communications, vol. 8, No. 4, 2002, pp. 369-374.
Laurent Saniere, et al, Regioselective Alkylations Of Optaically Active 4,5-Dihydro-1;,2,4-Triazin-6(1H)-Ones, Tetrahedron Letters 41 (2000) pp. 671-674.

* cited by examiner

*Primary Examiner*—Venkataraman Balasubramanian
(74) *Attorney, Agent, or Firm*—C. W. Arnett

(57) ABSTRACT

This invention relates to substituted dihydrotriazinones, triazinones and related compounds, compositions comprising such compounds and an agronomically acceptable carrier, and the use thereof as broad spectrum fungicides. This invention also teaches methods of preparing these compounds as well as methods of using the compounds as fungicides.

11 Claims, No Drawings

SUBSTITUTED 4,5-DIHYDRO-1,2,4-TRIAZIN-6-ONES, 1,2,4-TRIAZIN-6-ONES, AND THEIR USE AS FUNGICIDES

BACKGROUND OF THE INVENTION

This application claims the benefit of U.S. Provisional Application No. 60/677,434 filed on May 3, 2005. The present invention relates to dihydrotriazinones, triazinones and related compounds, compositions comprising such compounds, and the use thereof as broad spectrum fungicides.

Various triazinones are disclosed by Collins et al., Aust. J. Chem., 52, 379-385 (1999); Kanellakopulos et al. in U.S. Pat. No. 5,814,645; and by Sanière et al., in Tetrahedron Letters, 41, 671-674 (2000), however the compounds of the present invention and their uses are not disclosed. Other triazinones are presented in a review by Neunhoeffer et al., "Chemistry of 1,2,3-Triazines and 1,2,4-Triazines, Tetrazines, and Pentazines", 605-607, John Wiley and Sons, Inc., New York, N.Y. (1978), but no utility is suggested. Various aryl triazinones and aryl triazinophthalazines are disclosed by Kutscher et al. in ZA 938799, as drugs for the treatment of bronchial asthma and other conditions. WO 02/067675 discloses substituted 4,5-dihydro-1,2,4-triazin-6-ones, 1,2,4-triazin-6-ones, and their use as fungicides. However, it is well known that the fungicidal activity of chemical compounds is highly unpredictable and the compounds of the present invention are not disclosed or contemplated. Other publications have additionally disclosed similar chemistries, including U.S. Pat. No. 6,825,192 by Eisai and U.S. Pat. No. 6,159,980 by Dupont, however the compounds of the present invention are not disclosed.

SUMMARY OF THE INVENTION

The present invention relates to triazinones of the formula (I)

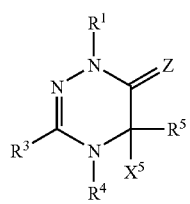

(I)

wherein the definitions are included herein; a composition comprising such compounds and a method of use as fungicides.

DETAILED DESCRIPTION

In one embodiment of the present invention, the invention relates to a compound of the formula (I)

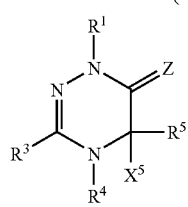

(I)

wherein
$R^1$ is selected from Group I or II; Group I consisting of:
alkyl, haloalkyl, cyanoalkyl, alkenyl, haloalkenyl, alkynyl, haloalkynyl, cycloalkylalkynyl, alkoxyalkyl, cycloalkyl, cycloalkylalkyl, trialkylsilylalkyl where the three alkyl groups may be the same or different, alkoxycarbonyl, alkylcarbonyl, alkoxycarbonylalkyl, phenyl optionally substituted with from one to three substituents independently selected from the group consisting of alkyl, halo, nitro, alkoxy, alkylthio, haloalkyl, haloalkylthio and haloalkoxy; phenalkyl optionally substituted on the phenyl ring with from one to three substituents independently selected from the group consisting of alkyl, halo, alkoxy, haloalkyl and haloalkoxy; pyridyl optionally substituted with from one to two substituents independently selected from the group consisting of alkyl and halo; furyl or thienyl, each optionally substituted with one to two substituents independently selected from halo and alkyl on the furyl or thienyl ring; and benzothienyl or benzofuranyl, each optionally substituted with one to two substituents independently selected from halo, alkyl and haloalkyl;

Group II consisting of:
a) aryloxyalkyl, haloalkoxyalkyl, haloalkoxyalkenyl, haloalkoxyalkynyl, trialkylsilylalkynyl where the three alkyl groups can be the same or different, substituted cycloalkylalkyl, cycloalkylalkenyl, cycloalkylcycloalkylalkyl, and cycloalkylalkylcycloalkylalkyl;
  wherein any cycloalkyl group above can be substituted with one to two substituents independently selected from the group consisting of alkylthio, haloalkyl, cyano, alkoxycarbonyl, alkoxycarbonylalkyl, alkoxycarbonylalkenyl, alkenoxycarbonyl, alkenoxycarbonylalkyl, alkenoxycarbonylalkenyl, alkylcarbonyl, alkylcarbonylalkyl, alkylcarbonylalkenyl, arylcarbonyl, arylcarbonylalkyl, arylcarbonylalkenyl, alkenylcarbonyl, alkenylcarbonylalkyl, alkenylcarbonylalkenyl, aryloxycarbonyl, aryloxycarbonylalkyl, aryloxycarbonylalkenyl, alkoxy, haloalkoxy, aryl, aralkyl, aralkenyl, heteroaryl, heteroarylalkyl, heteroarylalkenyl, heteroaryloxy, heteroaryloxyalkyl, and heteroaryloxyalkenyl,
    wherein any aryl or heteroaryl can be substituted with one to two substituents independently selected from the group consisting of alkyl, halo, alkoxy, haloalkyl, haloalkoxy, methylenedioxy and phenyl;
b) phenalkyl, optionally substituted on the phenyl ring with from four to five substituents independently selected from the group consisting of alkyl, halo, alkoxy, haloalkyl and haloalkoxy;
c) phenyl or phenalkyl, each substituted on the phenyl ring with one to two substituents independently selected from the group consisting of aryl, aryloxy, heteroaryl, heteroaryloxy, aralkyl, heteroarylalkyl, aryloxyalkyl and heteroaryloxyalkyl;
d) phenalkenyl, phenalkynyl, heteroarylalkyl, heteroarylalkenyl, and heteroarylalkynyl, wherein alkyl, alkenyl, alkynyl can be substituted with halogen, alkoxy, or aryloxy; and e) alkylcarbonyloxyalkyl, hydroxyalkyl, alkoxyalkyloxyalkyl, morpholinoalkyl, haloalkylcarbonyl, haloalkylcarbonylalkyl, alkenylcarbonylalkyl, haloalkenylcarbonylalkyl, alkynylcarbonylalkyl, haloalkynylcarbonylalkyl, arylcarbonylalkyl, aralkylcarbonylalkyl, aryloxyalkyl, alkylsulfonyloxyalkyl, heteroarylcarbonylalkyl, heteroarylalkylcarbonylalkyl, and arylaminocarbonyloxyalkyl;

wherein any aryl or heteroaryl can be substituted with one to two substituents independently selected from the group consisting of alkyl, halo, alkoxy, haloalkyl, haloalkoxy, methylenedioxy and phenyl;

$R^3$ is selected from Group III or Group IV, Group III consisting of:
a) alkyl, cycloalkyl, cycloalkylalkyl or phenalkyl optionally substituted on the phenyl ring with from one to three substituents independently selected from the group consisting of alkyl, halo, alkoxy, haloalkyl and haloalkoxy;
b) phenyl optionally substituted with from one to five substituents independently selected from the group consisting of
  1) halo, alkyl, haloalkyl, haloalkoxy, alkylthio, haloalkylthio, alkylsulfinyl, alkylsulfonyl, nitro, cyano;
  2) phenyl or phenoxy, each optionally substituted with one or two substituents on the phenyl ring, independently selected from the group consisting of halo, alkyl, alkoxy, haloalkyl, haloalkoxy, alkylthio, nitro and cyano; and
  3) dialkylamino, wherein the alkyl groups may be the same or different or together with the nitrogen to which they are attached form a 5- or 6-membered heterocyclic ring;
c) phenyl substituted solely with one heteroaryl group selected from the group consisting of:
  1) furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, and oxazol-5-yl;
    each optionally substituted with one or two substituents independently selected from halo, alkyl, alkoxy, haloalkoxy, haloalkyl, alkylthio, nitro and cyano; and
d) heteroaryl selected from furyl, thienyl, quinolinyl, isoquinolinyl, benzofuranyl, benzothienyl, pyridyl, pyridazinyl, pyrimidinyl, pyrazinyl, pyrazolyl, 1,2,3-thiadiazol-4-yl, thiazolyl, triazolyl, triazinyl, isoxazolyl and oxazolyl;
    each optionally substituted with one or two substituents independently selected from halo, alkyl, alkoxy, haloalkoxy, haloalkyl, alkylthio, haloalkylthio, nitro and cyano;
and Group IV consisting of:
  a) phenyl substituted with from one to three substituents independently selected from the group consisting of:
    hydroxyl, trihaloalkylsulfonyloxy, phenalkyl, phenalkenyl, phenalkynyl, indan-1-ylidenemethyl, phenalkoxy, phenylcarbonyl, phenalkenylcarbonyl, phencarbonylalkenyl, phen(alkoxyimino)methyl, phen(arylalkoxyimino)methyl, phencyclopropyl, phenylcyclopropylcarbonyl, phencarbonylcyclopropyl, phenaminocarbonyloxy, morpholinyl, heteroarylalkyl, heteroarylalkenyl, heteroarylcarbonyl, heteroaryloxy, where the heteroaryl ring and phenyl are substituted with from one to five substituents independently selected from the group consisting of:
      halo, alkyl, haloalkyl, haloalkoxy, alkylthio, haloalkylthio, alkylsulfinyl, alkylsulfonyl, nitro, phenyl, amino and cyano;
      and the phenyl ring of the indane can be further substituted with from one to five substituents independently selected from the group consisting of:
      halo, alkyl, haloalkyl, haloalkoxy, alkylthio, haloalkylthio, alkylsulfinyl, alkylsulfonyl, nitro and cyano;
  b) phenyl substituted with at least two substituents independently selected from the groups consisting of:
    i) a heteroaryl selected from furyl, thienyl, benzothienyl, pyridyl, pyridazinyl, pyrimidinyl, pyrazinyl, and oxazol-5-yl, optionally substituted with one or two substituents independently selected from halo, alkyl, alkoxy, haloalkoxy, haloalkyl, alkylthio, nitro and cyano; and
    ii) halo, alkyl, phenalkenyl;
    wherein at least one of the substituents is selected from i);
  c) heteroaryl selected from furyl, thienyl, pyridyl, pyridazinyl, pyrimidinyl, pyrazinyl, 1,2,3-thiadiazol-4-yl and oxazolyl, each substituted with one or two substituents independently selected from phenyl, phenalkyl, phenalkenyl, phenalkynyl, heteroaryl, where the phenyl or heteroaryl ring is substituted with from one to five substituents independently selected from the group consisting of halo, alkyl, haloalkyl, haloalkoxy, alkylthio, haloalkylthio, alkylsulfinyl, alkylsulfonyl, nitro and cyano;
  d) aryloxy, heteroaryloxy, aryloxyalkyl, heteroaryloxyalkyl; each optionally substituted on the aryl or heteroaryl ring with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring;
  e) aryloxy, heteroaryloxy, aryloxyalkyl, heteroaryloxyalkyl substituted with a heteroaryl group selected from the group consisting of furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, and oxazol-5-yl;
    each optionally substituted with one or two substituents independently selected from halo, alkyl, alkoxy, haloalkoxy, haloalkyl, alkylthio, nitro and cyano; and
  f) arylcarbonyl, arylthio, arylamino, arylcarbonylalkyl, arylthioalkyl, arylaminoalkyl, heteroarylcarbonyl, heteroarylthio, heteroarylamino, heteroarylcarbonylalkyl, heteroarylthioalkyl, heteroarylaminoalkyl, arylcarbonyloxy, arylcarbonyloxyalkyl, arylcarbonylthio, arylcarbonylthioalkyl, arylcarbonylamino, arylcarbonylaminoalkyl;

$R^4$ is selected from the group consisting of:
  a) a hydrogen atom, alkylcarbonyl, alkylcarbonylalkyl, cycloalkylcarbonyl, alkylsulfonyl, alkylthio, amino, alkylamino, dialkylamino wherein the alkyl groups may be the same or different or together with the nitrogen to which they are attached form a 5- or 6-membered heterocyclic ring, cyano, alkenylsulfonyl, alkenylcarbonyl, alkoxycarbonyl, haloalkoxycarbonyl, alkoxycarbonylalkyl, alkoxycarbonylthio, (alkylthio)carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxycarbonyl; and
  b) aralkyl, arylcarbonyl, arylsulfonyl, arylsulfonylalkenyl, aryloxycarbonyl, aryloxythiocarbonyl, arylthiothiocarbonyl; each substituted on the aromatic ring with one to two substituents independently selected from halo and alkyl;

$R^5$ is selected from the group consisting of:
  a) a hydrogen atom, alkylcarbonyl, alkylcarbonylalkyl, formyl, alkoxy, alkoxycarbonyl, alkoxycarbonyloxy, alkylcarbonyloxy, alkylcarbonyloxyalkyl, alkoxycarbonylthio, alkylcarbonylthio, alkylthio, haloalkylthio, hydroxy, mercapto, carboxyalkylthio, hydroxyalkylthio, cycloalkyloxy, cycloalkylthio, carboxyalkylthio, cyano, amino; and
  b) aryloxy, arylthio, aralkyloxy, aralkylthio or arylcarbonylthio; each optionally substituted on the aryl ring with from one to three substituents independently selected from the group consisting of alkyl, halo, alkoxy, haloalkyl, haloalkoxy, amino, alkylamino and dialkylamino wherein the alkyl groups may be the same or different or together with the nitrogen to which they are attached form a 5- or 6-membered heterocyclic ring; or $R^4$ can form a fused ring to the $R^3$ substituent when the $R^3$ substituent is aryl or heteroaryl wherein $R^4$ is selected from —CH(R)—, —O—, —S—, —N(R)—, —C(=O)—, —O(C=O)—, —C(=O)O—, —CH$_2$CH$_2$—, —CH=CH—, —N(R)CH$_2$—, —CH(R)O—, —OCH(R)—, —CH(R)S— and —SCH(R)—;

with the proviso that when $R^5$ is a hydrogen atom, alkylcarbonyl, alkylcarbonylalkyl, formyl, alkoxy, alkoxycarbonyl, alkoxycarbonyloxy, alkylcarbonyloxy, alkoxycarbonylthio, alkylcarbonylthio, alkylthio, hydroxy, mercapto, alkenyl, alkynyl, cyano, amino, aryloxy, arylthio, or arylcarbonylthio; and 1) $R^1$ is selected from Group I, then $R^3$ is selected from Group IV, or
2) when $R^3$ is selected from Group III, then $R^1$ is selected from Group II;

$X^5$ is a hydrogen atom or taken together with $R^4$ forms a nitrogen-carbon bond, Z is an oxygen atom, a sulfur atom or NR, R is H or alkyl, or an agronomically acceptable salt, isomer, tautomer, enantiomer and mixture thereof, provided that:

when $R^1$ is an aralkyl or a heteroarylalkyl, $R^4$ is not cyano, alkylsulfonyl, arylsulfonyl or polyhaloalkyl;

when $R^3$ is phenyl, $R^1$ is not benzyl or benzyloxymethyl;

when $R^1$ is hydroxyalkyl, $R^3$ is not chloropyridyl;

when $R^1$ is morpholinoalkyl, $R^3$ is not unsubstituted phenyl;

when $R^3$ is arylcarbonyl, $R^1$ is not phenyl or substituted phenyl; and when $X^5$ is taken together with $R^4$ to form a nitrogen-carbon bond, $R^5$ is H.

Preferably, $R^4$ and $X^5$ are each H; $R^5$ is selected from the group consisting of a hydrogen atom, alkylcarbonyl, haloalkylthio, hydroxyalkylthio, cycloalkyloxy, cycloalkylthio, carboxyalkylthio, aryloxy and arylthio; and Z is O.

The term "alkenyl" refers to an ethylenically unsaturated $C_2$-$C_{12}$ hydrocarbon group, straight or branched chain, having 1 or 2 ethylenic bonds; for example vinyl, allyl, 1-butenyl, 2-butenyl, isopropenyl, 2-pentenyl, allenyl and the like.

The term "alkenyloxycarbonyl" or "alkenoxycarbonyl" refers to an alkenyloxy group attached to a carbonyl group (alkenyl-O—C(O)—); for example allyloxycarbonyl, vinyloxycarbonyl and the like.

The term "alkenoxycarbonylalkenyl" refers to an alkenyl group substituted with an alkenyloxycarbonyl(alkenyl-O—C(O)-alkenyl-); for example 3-(allyloxycarbonyl)-2-propenyl, 3-(vinyloxycarbonyl)-2-propenyl and the like.

The term "alkenoxycarbonylalkyl" refers to an alkyl group substituted with an alkenyloxycarbonyl(alkenyl-O—C(O)-alkyl-); for example 3-(allyloxycarbonyl)propyl, 2-(vinyloxycarbonyl)propyl and the like.

The term "alkenylcarbonyl" refers to an alkenyl group attached to a carbonyl group (alkenyl-C(O)—); for example allylcarbonyl, 1-butenylcarbonyl, isopropenylcarbonyl and the like.

The term "alkenylcarbonylalkenyl" refers to an alkenyl group substituted with an alkenylcarbonyl(alkenyl-C(O)-alkenyl-); for example 3-(allylcarbonyl)-2-propenyl, 4-(vinylcarbonyl)-2-butenyl and the like.

The term "alkenylcarbonylalkyl" refers to an alkyl group substituted with an alkenylcarbonyl(alkenyl-C(O)-alkyl-); for example allylcarbonylmethyl, 3-(vinylcarbonyl)propyl and the like.

The term "alkenylsulfonyl" refers to an alkenyl group attached to a sulfonyl group, (alkenyl-SO$_2$—).

The term "alkenylthio" refers to an alkenyl group attached to a thio group(alkenyl-S—).

The term "alkenylthiothiocarbonyl" refers to an alkenylthio functionality attached to a thiocarbonyl group (alkenyl-S—C(S)—); for example allylthiothiocarbonyl and the like.

The term "alkoxy" refers to an alkyl group attached to a terminal oxygen atom (alkyl-O—). Typical alkoxy groups include methoxy, ethoxy, n-propoxy, isopropoxy, tert-butoxy and the like.

The term "alkoxyalkyl" refers to an alkyl group substituted with an alkoxy group (alkyl-O-alkyl-); for example isopropoxymethyl.

The term "alkyloxyalkyloxyalkyl" refers to an alkyl group substituted with an alkoxyalkyl group which is attached to an oxygen (alkyl-O-alkyl-O-alkyl-) or to a di(alkyloxy)alkyloxyalkyl group; for example isopropoxymethoxymethyl and the like.

The term "alkoxycarbonyl" refers to an alkoxy attached to a carbonyl group (alkyl-O—C(O)—); for example ethoxycarbonyl, methoxycarbonyl and the like.

The term "alkoxycarbonylalkyl" refers to an alkyl group substituted with an alkoxycarbonyl(alkyl-O—C(O)-alkyl-); for example ethoxycarbonylmethyl, 2-(methoxycarbonyl)propyl and the like.

The term "alkoxycarbonylalkenyl" refers to an alkenyl group substituted with an alkoxycarbonyl(alkyl-O—C(O)-alkenyl-); for example 3-(ethoxycarbonyl)-2-propenyl, 4-(methoxycarbonyl)-2-butenyl and the like.

The term "alkoxycarbonyloxy" refers to an alkoxy group attached to a carbonyl group which is in turn attached to a oxygen atom (alkyl-O—C(O)—O—); for example ethoxycarbonyloxy, methoxycarbonyloxy and the like.

The term "alkoxycarbonylthio" refers to an alkoxy group attached to a carbonyl group which is in turn attached to a sulfur atom (alkyl-O—C(O)—S—); for example ethoxycarbonylthio, methoxycarbonylthio and the like.

The term "alkoxyoxalyl" refers to an alkoxy group attached to a oxalyl group (alkyl-O—C(O)—C(O)—); for example ethoxyoxalyl, methoxyoxalyl and the like.

The term "alkyl" refers to a $C_1$-$C_{12}$ saturated hydrocarbon group, straight or branched, for example methyl, ethyl, propyl, isopropyl, n-butyl, sec-butyl, isobutyl, tert-butyl, n-pentyl, isopentyl, n-hexyl, n-heptyl, isooctyl, nonyl, decyl, undecyl, dodecyl and the like.

The term "alkylamino" refers to an alkyl group attached to a nitrogen atom (alkyl-NR—, wherein R is H or alkyl); for example methylamino, isopropylamino and the like.

The term "alkylaminocarbonyl" refers to an alkylamino group attached to a carbonyl group (alkyl-NR—C(O)—, wherein R is H or alkyl); for example methylaminocarbonyl, isopropylaminocarbonyl and the like.

The term "alkylcarbonyl" refers to an alkylketo functionality (alkyl-C(O)—); for example acetyl, n-butyryl and the like.

The term "alkylcarbonylalkenyl" refers to an alkenyl group substituted with an alkylcarbonyl(alkyl-C(O)-alkenyl-); for example 3-acetyl-2-propenyl, 4-butyryl-2-butenyl and the like.

The term "alkylcarbonylalkyl" refers to an alkylketoalkyl functionality (alkyl-C(O)-alkyl-); for example acetylmethyl and the like.

The term "alkylcarbonyloxy" refers to an alkyl group attached to a carbonyl group which is in turn attached to a oxygen atom (alkyl-C(O)—O—); for example acetoxy, tert-butylcarbonyloxy and the like.

The term "alkylcarbonyloxyalkoxycarbonyl" refers to an acyloxyalkoxycarbonyl (alkyl-C(O)—O-alkyl-O—C(O)—); for example acetoxymethoxycarbonyl and the like.

The term "alkylcarbonyloxyalkyl" refers to an alkyl group substituted with an alkylcarbonyloxy(alkyl-C(O)—O-alkyl-); for example acetoxymethyl, 3-(tert-butylcarbonyloxy)propyl and the like.

The term "alkylcarbonylthio" refers to an alkyl group attached to a carbonyl group which is in turn attached to a sulfur atom (alkyl-C(O)—S—); for example ethylcarbonylthio, methylcarbonylthio and the like.

The term "alkylsulfinyl" refers to a sulfinyl moiety substituted with an alkyl group (alkyl-SO—); for example methylsulfinyl, n-propylsulfinyl and the like.

The term "alkylsulfonyl" refers to a sulfonyl moiety substituted with an alkyl group (alkyl-SO$_2$—); for example mesyl, n-propylsulfonyl and the like.

The term "alkylthio" refers to an alkyl group attached to a sulfur atom (alkyl-S—); for example methylthio.

The term "alkyl(thiocarbonyl)" refers to an alkyl group attached to a thiocarbonyl group (alkyl-C(S)—); for example thioacetyl and the like.

The term "(alkylthio)carbonyl" refers to an alkylthio group attached to a carbonyl group (alkyl-S—C(O)—); for example methylthiocarbonyl and the like.

The term "alkylthiothiocarbonyl" refers to an alkylthio group attached to a thiocarbonyl group (alkyl-S—C(S)—); for example propylthiothiocarbonyl and the like.

The term "alkynyl" refers to an unsaturated $C_2$-$C_{12}$ hydrocarbon group, straight or branched, having 1 or 2 acetylenic bonds; for example ethynyl, propargyl and the like.

The term "alkynylcarbonyl" refers to an alkynyl group attached to a carbonyl group (alkynyl-C(O)—); for example ethynylcarbonyl, propargylcarbonyl and the like.

The term "alkynylcarbonylalkyl" refers to an alkyl group substituted with an alkynylcarbonyl(alkynyl-C(O)-alkyl-); for example ethynylcarbonylmethyl, 3-(propargylcarbonyl)propyl and the like.

The term "alkynyloxycarbonyl" refers to an alkynyloxy attached to a carbonyl group (alkynyl-O—C(O)—); for example propargyloxycarbonyl and the like.

The term "alkynylthiothiocarbonyl" refers to an alkynylthio group attached to a thiocarbonyl group (alkynyl-S—C(S)—); for example propargylthiothiocarbonyl and the like.

The term "amino" refers to a —NH$_2$, —NHR or —NR$_2$ group wherein R is independently alkyl, alkenyl or alkynyl.

The term "aralkyl" refers to an alkyl group substituted with an aryl ring, with the aryl forming a terminal portion of the aralkyl moiety (Ar-alkyl-, wherein Ar is an aryl ring). Examples of aralkyl groups include, but are not limited to, benzyl, phenethyl and the like.

The term "aralkenyl" refers to an alkenyl group substituted with an aryl ring, with the aryl forming a terminal portion of the aralkenyl moiety (Ar-alkenyl-).

Examples of aralkenyl groups include, but are not limited to, styryl and phenyl-2-propenyl and the like.

The term "aralkylcarbonyl" refers to an aralkylgroup attached to a carbonyl group (Ar-alkyl-C(O)—); for example benzylcarbonyl and the like.

The term "aralkylcarbonylalkyl" refers to an alkyl group substituted with an aralkylcarbonyl(Ar-alkyl-C(O)-alkyl-); for example 4-methylbenzylcarbonylmethyl, 3-(2-phenylethyl-carbonyl)propyl and the like.

The term "aralkyloxy" refers to an aralkyl group which is attached to an oxygen (Ar-alkyl-O—). Examples of aralkyloxy groups include benzyloxy, phenylethoxy and the like.

The term "aralkylthio" refers to an aralkyl group which is attached to a sulfur (Ar-alkyl-S—). Examples of aralkylthio groups include as benzylthio, phenylethylthio and the like.

The term "aryl" refers to an aromatic ring structure; for example phenyl, naphthyl and the like.

The term "arylamino" refers to an aryl group attached to a nitrogen atom (Ar—NR—, wherein R is H, alkyl, alkenyl or alkynyl); for example phenylamino and the like.

The term "arylaminoalkyl" refers to an alkyl group substituted with an arylaminogroup (Ar—NR-alkyl-, wherein R is H, alkyl, alkenyl or alkynyl); for example anilinomethyl, and the like.

The term "arylaminocarbonyl" refers to an arylamino group attached to a carbonyl group (Ar—NR—C(O)—, wherein R is H, alkyl, alkenyl or alkynyl); for example phenylaminocarbonyl and the like.

The term "arylaminocarbonyloxyalkyl" refers to an alkyl group attached to an oxygen which is attached to an arylaminocarbonyl(Ar—NR—C(O)—O-alkyl-, wherein R is H, alkyl, alenyl or alkynyl); for example phenylaminocarbonyloxymethyl and the like.

The term "arylcarbonyl" refers to an arylketo functionality (Ar—C(O)—); for example benzoyl and the like.

The term "arylcarbonylalkenyl" refers to an alkenyl group attached to the carbonyl of an aryl carbonyl group (Ar—C(O)-alkenyl-); for example 3-benzoyl-2-propenyl and the like.

The term "arylcarbonylalkyl" refers to an alkyl group attached to the carbonyl of an aryl carbonyl group (Ar—C(O)-alkyl-); for example 2-benzoylethyl and the like.

The term "arylcarbonylamino" refers to an arylcarbonyl group attached to a nitrogen atom (Ar—C(O)—NR—, wherein R is H, alkyl, alkenyl or alkynyl); for example benzoylamino and the like.

The term "arylcarbonylaminoalkyl" refers to an alkyl group attached to the nitrogen of an arylcarbonylamino (Ar—C(O)—NR-alkyl-, wherein R is H, alkyl, alkenyl or alkynyl); for example 2-benzoylaminoethyl and the like.

The term "arylcarbonyloxy" refers to an aryl group attached to a carbonyl group which is in turn attached to a oxygen atom (Ar—C(O)—O—); for example benzoyloxy and the like.

The term "arylcarbonyloxyalkyl" refers to an alkyl group substituted with a arylcarbonyloxy(Ar—C(O)—O-alkyl-), for example, benzoyloxymethyl and the like.

The term "arylcarbonylthio" refers to an aryl group attached to a carbonyl group which is in turn attached to a sulfur atom (Ar—C(O)—S—); for example phenylcarbonylthio and the like.

The term "arylcarbonylthioalkyl" refers to an alkyl group substituted with an arylcarbonylthio(Ar—C(O)—S-alkyl-); for example, phenylcarbonylthioethyl and the like.

The term "aryloxy" refers to an aryl group attached to an oxygen atom (Ar—O—); for example phenoxy and the like.

The term "aryloxyalkyl" refers to an alkyl group substituted with an aryloxy (Ar—O-alkyl-); for example, phenoxymethyl, phenoxyethyl and the like.

The term "aryloxycarbonyl" refers to an aryloxy attached to a carbonyl group (Ar—O—C(O)—); for example phenoxycarbonyl and the like.

The term "aryloxycarbonylalkenyl" refers to an alkenyl group substituted with an aryloxycarbonyl(Ar—O—C(O)-alkenyl-); for example, 3-(phenoxycarbonyl)-2-propenyl, and the like.

The term "aryloxycarbonylalkyl" refers to an alkyl group substituted with an aryloxycarbonyl(Ar—O—C(O)-alkyl-); for example, phenoxycarbonylmethyl, 2-(phenoxycarbonyl) ethyl, and the like.

The term "aryloxythiocarbonyl" refers to an aryloxy group attached to a thiocarbonyl group (Ar—O—C(S)—); for example phenoxythiocarbonyl and the like.

The term "arylsulfonyl" refers to a sulfonyl group substituted with an aryl group (Ar—SO—); for example toluenesulfonyl and the like.

The term "arylsulfonylalkenyl" refers to an alkenyl group substituted with an arylsulfonyl group (Ar—SO-alkenyl-).

The term "arylthio" refers to an aryl group attached to a sulfur atom (Ar—S—); for example phenylthio and the like.

The term "arylthioalkyl" refers to an alkyl group substituted with an arylthio group (Ar—S-alkyl-); for example phenylthiomethyl and the like.

The term "arylthiothiocarbonyl" refers to an arylthio group attached to a thiocarbonyl group (Ar—S—C(S)—); for example phenylthiothiocarbonyl and the like.

The term "carboxyalkylthio" refers to a carboxyl group attached the alkyl of an alkylthio group (HOOC-alkyl-S—); for example carboxymethylthio, carboxyethylthio and the like.

The term "cyano" refers to a carbon atom triple bonded to a nitrogen atom (—C≡N).

The term "cyanoalkyl" refers to an alkyl group substituted with a cyano group (N≡C-alkyl-); for example cyanomethyl, 2-cyanoethyl and the like.

The term "cycloalkyl" refers to a cyclic $C_3$-$C_{10}$ aliphatic ring structure; for example cyclopropyl, cyclobutyl, cyclopentyl, cyclohexyl, cycloheptyl, cyclooctyl and the like.

The term "cycloalkylalkenyl" refers to an alkenyl group substituted with a cycloalkyl group (cycloalkyl-alkenyl-); such as 3-cyclopropyl-2-propenyl, 2-cyclobutyl-2-propenyl and the like.

The term "cycloalkylalkyl" refers to a cycloalkyl group attached to an alkyl group (cycloalkyl-alkyl-); for example cyclopropylmethyl, 2-cyclopropylethyl, cyclohexylethyl and the like.

The term "cycloalkylalkylcycloalkyl" refers to a cycloalkylalkyl group attached via the alkyl to a cycloalkyl group (cycloalkyl-alkyl-cycloalkyl-); for example cyclopropyl-methylcyclopropyl, 2-(2-cyclopropylethyl)cyclopropyl, 2-(cyclohexylmethyl)-cyclopropyl and the like.

The term "cycloalkylalkylcycloalkylalkyl" refers to a cycloalkylalkylcycloalkyl group attached via the cycloalkyl to an alkyl group (cycloalkyl-alkyl-cycloalkyl-alkyl-); for example cyclopropylmethylcyclopropylmethyl, 2-(2-cyclopropylethyl)cyclopropyl-methyl, 2-(cyclohexylmethyl)cyclopropylmethyl and the like.

The term "cycloalkylalkynyl" refers to a cycloalkyl group attached to an alkynyl group (cycloalkyl-alkynyl-); for example cyclopropylpropargyl, 4-cyclopentyl-2-butynyl and the like.

The term "cycloalkylcarbonyl" refers to a cycloalkylketo group (cycloalkyl-C(O)—); for example cyclopropylcarbonyl and the like.

The term "cycloalkylcycloalkyl" refers to a cycloalkyl group attached to a cycloalkyl group (cycloalkyl-cycloalkyl-); for example, 2-(cyclopropyl)cyclopropyl, 1-(cyclohexyl)cyclopropyl and the like.

The term "cycloalkylcycloalkylalkyl" refers to an alkyl group attached to a cycloalkylcycloalkyl group (cycloalkyl-cycloalkyl-alkyl-); for example, 2-(cyclopropyl)cyclopropylmethyl, 2-((1-cyclopropyl)cyclopropyl)ethyl and the like.

The term "cycloalkyloxy" refers to a cycloalkyl group attached to an on oxygen (cycloalkyl-O—); for example cyclohexyloxy, cyclopentyloxy and the like The term "cycloalkylthio" refers to a cycloalkyl group attached to a thio group (cycloalkyl-S—); for example cyclohexylthio, cyclopentylthio, cyclopropylthio and the like.

The term "dialkylamino" refers to two alkyl groups, which may be the same or different, attached to a nitrogen atom (R(R')N—, wherein R and R' are independently alkyl); for example dimethylamino, N-ethyl-N-methylamino and the like.

The term "dialkylaminocarbonyl" refers to a dialkylamino group attached to a carbonyl group (R(R')N—C(O)—, wherein R and R' are independently alkyl); for example dimethylaminocarbonyl and the like.

The term "formyl" refers to HC(O)—.

The term "halo" refers to fluoro, chloro, bromo or iodo.

The term "haloalkenyl" refers to an alkenyl group substituted with one or more halo groups (($X)_n$-alkenyl, wherein X is halo and n is 1, 2, or 3).

The term "haloalkenylcarbonyl" refers to a haloalkenyl group attached to a carbonyl group (($X)_n$-alkenyl-C(O)—, wherein X is halo and n is 1, 2, or 3); for example 1,2,2-trifluoroethenylcarbonyl, and the like.

The term "haloalkenylcarbonylalkyl" refers to an alkyl group attached to the carbonyl of a haloalkenylcarbonyl (($X)_n$-alkenyl-C(O)-alkyl-, wherein X is halo and n is 1, 2, or 3), for example 3-fluoro-2-propenylcarbonylmethyl and the like.

The term "haloalkoxy" refers to an alkoxy group substituted with one or more halo groups (($X)_n$-alkyl-O—, wherein X is halo and n is 1, 2, or 3); for example chloromethoxy, trifluoromethoxy, difluoromethoxy, perfluoroisobutoxy and the like.

The term "haloalkoxyalkenyl"" refers to an alkenyl group substituted with a haloalkoxy (($X)_n$-alkyl-O-alkenyl, wherein X is halo and n is 1, 2, or 3); for example, 1-trifluoromethoxy-2-propenyl and the like.

The term "haloalkoxyalkyl" refers to an alkyl group substituted with a haloalkoxy (($X)_n$-alkyl-O-alkyl-, wherein X is halo and n is 1, 2, or 3); for example, 3-trifluoro-methoxymethyl and the like.

The term "haloalkoxyalkynyl" refers to an alkynyl group substituted with a haloalkoxy (($X)_n$-alkyl-O-alkynyl-, wherein X is halo and n is 1, 2, or 3); for example, 3-trifluoromethoxypropargyl and the like.

The term "haloalkoxycarbonyl" refers to an alkoxy group substituted with one or more halo groups attached to a carbonyl group (($X)_n$-alkyl-O—C(O)—, wherein X is halo and n is 1, 2, or 3); for example chloromethoxycarbonyl, trifluoromethoxycarbonyl, difluoromethoxy-carbonyl, perfluoroisobutoxycarbonyl and the like.

The term "haloalkyl" refers to an alkyl group substituted with one or more halo groups (($X)_n$-alkyl-, wherein X is halo and n is 1, 2, or 3); for example chloromethyl, 2-bromoethyl, 3-iodopropyl, trifluoromethyl, 2,2,2-trifluoroethyl, perfluoropropyl, 8-chlorononyl and the like.

The term "haloalkylcarbonyl" refers to an alkyl group substituted with one or more halo groups attached to a carbonyl group(($X)_n$-alkyl-C(O)—, wherein X is halo and n is 1, 2, or 3); for example chloromethylcarbonyl, trifluoromethylcarbonyl, difluoromethylcarbonyl, perfluoroisobutylcarbonyl and the like.

The term "haloalkylcarbonylalkyl" refers to an alkyl group attached to the carbonyl of a haloalkylcarbonyl $((X)_n$-alkyl-C(O)-alkyl-, wherein X is halo and n is 1, 2, or 3); for example chloromethylcarbonylmethyl, trifluoromethylcarbonylethyl and the like.

The term "haloalkylthio" refers to an alkylthio group substituted with one or more halo groups $((X)_n$-alkyl-S—, wherein X is halo and n is 1, 2, or 3), for example trifluoromethylthio and the like.

The term "haloalkynyl" refers to an alkynyl group substituted with one or more halo groups($(X)_n$-alkynyl-, wherein X is halo and n is 1, 2, or 3).

The term "haloalkynylcarbonyl" refers to an alkynyl group, substituted with one or more halo groups, attached to a carbonyl group $((X)_n$-alkynyl-C(O)—, wherein X is halo and n is 1, 2, or 3); for example chloroethynylcarbonyl, 3-fluoro-2-propynyl-carbonyl and the like.

The term "haloalkynylcarbonylalkyl" refers to an alkyl group attached to the carbonyl of a haloalkynyllcarbonyl $((X)_n$-alkynyl-C(O)-alkyl-, wherein X is halo and n is 1, 2, or 3) for example chloroethynylcarbonylmethyl, 3-fluroro-2-propynylcarbonylmethyl and the like.

The term "heteroaryl" refers to a 5 or 6 membered unsaturated ring containing one, two or three heteroatoms, preferably one or two heteroatoms independently selected from oxygen, nitrogen and sulfur or to a bicyclic unsaturated ring system containing up to 10 atoms including one heteroatom selected from oxygen, nitrogen and sulfur. Examples of heteroaryls include, but are not limited to, 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzofuranyl and benzothiofuranyl (benzothienyl) and the like.

The term "heteroarylalkenyl" refers to an alkenyl group substituted with a heteroaryl which forms a terminal portion of the heteroarylalkenyl moiety (heteroaryl-alkenyl-); for example 3-furylethenyl, 3-(3-thienyl)-2-propenyl, 1-(3-pyridyl)-2-propenyl and the like.

The term "heteroarylalkyl" refers to an alkyl group substituted with a heteroaryl which forms a terminal portion of the heteroarylalkyl moiety (heteroaryl-alkyl-); for example 3-furylmethyl, 3-thienylmethyl, 2-(3-pyridyl)ethyl and the like.

The term "heteroarylalkylcarbonylalkyl" refers to an alkyl group substituted with an alkylcarbonyl group which is also attached to a heteroarylalkyl group (heteroaryl-alkyl-C(O)-alkyl-); for example 3-furylmethylcarbonylmethyl, 2-(3-pyridyl)ethyl-carbonylethyl and the like.

The term "heteroarylalkylheteroarylalkenyl" refers to a heteroarylalkenyl group further substituted with heteroarylalkyl (heteroaryl-alkyl-hetaryl-alkenyl-).

The term "heteroarylalkynyl" refers to an alkynyl group substituted with a heteroaryl, which forms the terminal portion of the heteroarylalkynyl moiety (heteroaryl-alkynyl-); for example 3-(3-furylmethyl)-2-propynyl, 4-(3-pyridyl)-2-butynyl and the like.

The term "heteroarylamino" refers to a heteroaryl group attached to a nitrogen atom; for example 3-pyridylamino, 2-thienylamino and the like.

The term "heteroarylaminoalkyl" refers to an alkyl group substituted with heteroarylamino which forms the terminal portion of the heteroarylaminoalkyl moiety (heteroaryl-amino-alkyl-); for example 3-pyridylaminomethyl, 2-thienylaminomethyl 2-(3-pyridyl)aminoethyl and the like.

The term "heteroarylcarbonyl" refers to a heteroaryl group attached to a carbonyl group (heteroaryl-C(O)—); for example 3-pyridylcarbonyl, 2-thienylcarbonyl, 2-isoxazolylarbonyl and the like.

The term "heteroarylcarbonylalkyl" refers to an alkyl group substituted with heteroarylcarbonyl which forms the terminal portion of the heteroarycarbonylalkyl moiety (heteroaryl-C(O)-alkyl-); for example 3-pyridylcarbonylmethyl, 2-thienyl-carbonylmethyl, 2-(2-isoxazolylcarbonyl)ethyl, and the like.

The term "heteroaryloxy" refers to a heteroaryl group attached to an oxygen atom (heteroaryl-O—); for example 3-pyridyloxy, 2-thienyloxy, 5-pyrimidinyloxy and the like.

The term "heteroaryloxyalkenyl" refers to an alkenyl group substituted with a heteroaryloxy(heteroaryl-O-alkenyl-); for example, 3-(3-pyridyloxy)-2-propenyl, 1-(2-thienyloxy)-2-propenyl and the like.

The term "heteroaryloxyalkyl" refers to an alkyl group substituted with a heteroaryloxy(heteroaryl-O-alkyl-); for example, 3-(3-pyridyloxy)propyl 2-(2-thienyloxy)propyl, 2-(5-pyrimidinyloxy)ethyl and the like.

The term "heteroarylthio" refers to a heteroaryl group attached to a sulfur atom (heteroaryl-S—); for example 3-pyridylthio, 2-thienylthio, 5-pyrimidinylthio and the like.

The term "heteroarylthioalkyl" refers to an alkyl group substituted with a heteroarylthio(heteroaryl-S-alkyl-); for example, 3-(3-pyridylthio)propyl, 2-(2-thienylthio)propyl, 2-(5-pyrimidinylthio)ethyl and the like.

The term "hydroxyalkyl" refers to an alkyl group substituted with a hydroxyl group (HO-alkyl-); for example 2-hydroxyethyl, 3-hydroxypropyl, 2-hydroxypropyl and the like.

The term "hydroxyalkylthio" refers to a hydroxyl group attached to the alkyl of an alkylthio group (HO-alkyl-S—); for example 2-hydroxyethylthio and the like.

The term "hydroxyl" refers to HO—.

The term "mercapto" refers to HS—.

The term "morpholinoalkyl" refers to an alkyl group attached to a morpholino group via the morpholino nitrogen (morpholino-alkyl-); for example 2-(N-morpholino)ethyl, 3-(N-morpholino)propyl and the like.

The term "nitro" refers to a moiety attached via the nitrogen atom and bonded to 2 oxygen atoms with a neutral charge (—$NO_2$).

The term "phenalkenyl" or "phenylalkenyl" refers to an alkenyl group substituted with phenyl which forms the terminal portion of the phenalkenyl moiety (phenyl-alkenyl-). Examples of phenalkenyl groups include, but are not limited to, styryl and phenyl-2-propenyl and the like.

The term "phenalkenylcarbonyl" refers to a phenalkenyl group attached to a carbonyl group (phenyl-alkenyl-C(O)—); for example styrylcarbonyl, phenyl-2-propenylcarbonyl and the like.

The term "phenalkoxy" refers to a phenalkyl group attached to an oxygen (phenyl-alkyl-O—). Examples of phenalkoxy groups include, as benzyloxy and the like.

The term "phen(alkoximino)methyl" refers to a group wherein an imino group is attached to a phenyl via the carbon of the imino group and the oxygen is attached to an alkyl group (phenyl-C(=N—O-alkyl-)methyl). Examples of phen(alkoximino)methyl groups include, as phenylmethoxyiminomethyl and the like.

The term "phenalkyl" refers to an alkyl group substituted with phenyl which forms the terminal portion of the phenalkyl moiety (phenyl-alkyl-). Examples of phenalkyl groups include, but are not limited to, benzyl and phenethyl and the like.

The term "phen(arylalkyloxyimino)methyl" or "phen(aralkoxyimino)methyl?" refers to a group wherein an imino group is attached to a phenyl via the carbon of the imino group and the oxygen is attached to an arylalkyloxy group (phenyl-C(=N—O-alkylphenyl)methyl). Examples of phen(arylalkyloxyimino) groups include, as phenyl(benzyloxy)iminomethyl and the like.

The term "phenalkynyl" or "phenylalkynyl" refers to an alkynyl group substituted with a phenyl which forms a terminal portion of the phenalkynyl moiety (phenyl-alkynyl-). Examples of phenalkynyl groups include, but are not limited to, phenylethynyl, 3-phenyl-2-propynyl and the like.

The term "phenaminocarbonyloxy" refers to Ar—NR—C(O)—O-wherein R is H, alkyl, alkenyl or alkynyl); for example (2,6-dichlorophenylaminocarbonyloxy) and the like.

The term "phencarbonyl" or "phenylcarbonyl" refers to a carbonyl group which is substituted with a phenyl (phenyl-C(O)—).

The term "phencarbonylalkenyl" refers to an alkenyl group substituted with a phencarbonyl group (phenyl-C(O)-alkenyl-); for example styrylcarbonyl, phenyl-2-propenylcarbonyl and the like.

The term "phencarbonylcyclopropyl" refers to a cyclopropyl group which is substituted with a phencarbonyl group (phenyl-C(O)-cyclopropyl-).

The term "phencyclopropyl" refers to a cyclopropyl group which is substituted with a phenyl group (phenyl-cyclopropyl-).

The term "phenoxy" refers to a phenyl group attached to an oxygen atom (phenyl-O—); for example phenoxy.

The term "phenylcyclopropylcarbonyl" refers to a carbonyl group substituted with a phencyclopropylgroup (phenyl-cyclopropyl-C(O)—).

The term "polyhaloalkyl" refers to an alkyl group which is substituted with more than one halogen, wherein the halogen may be the same or different.

The term "pyridyl" refers to a pyridine ring directly attached (pyridyl-).

The term "sulfonyloxy" refers to an oxygen atom attached to a sulfonyl group ($SO_2$—O—).

The term "trialkylsilylalkyl" refers to three alkyl groups, which may be the same or different, attached to a silicon atom which is in turn attached to an alkyl group ($R_3$—Si-alkyl-, wherein R is alkyl); for example trimethylsilylmethyl.

The term "trialkylsilylalkynyl" refers to three alkyl groups, which may be the same or different, attached to a silicon atom which is in turn attached to an alkynyl group ($R_3$—Si-alkynyl-, wherein R is alkyl); for example trimethylsilylpropargyl and the like.

The term "trihaloalkylsulfonyloxy" refers to a sulfonyloxy group which is substituted with a trihaloalkyl group (($X)_3$-alkyl-$SO_2$—O—).

The compounds of formula (I) also embrace tautomeric forms, for example

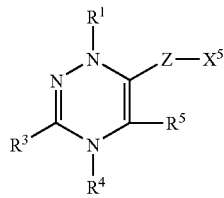

wherein $X^5$ is a hydrogen atom and $R^1$, $R^3$, $R^4$, $R^5$ and Z are as previously defined.

A second embodiment of the present invention relates to a fungicidal composition comprising a fungicidally effective amount of a compound of the formula (I)

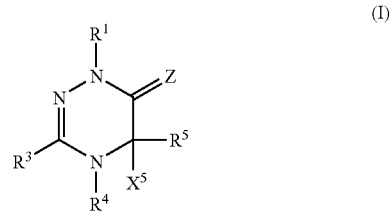

(I)

wherein $R^1$, $R^3$, $R^4$, $R^5$ and Z are as previously defined, or an agronomically acceptable salt, isomers, tautomer, enantiomer and mixture thereof, and an agronomically acceptable carrier.

Another embodiment of the present invention relates to a method of controlling a fungus comprising applying a fungicidally effective amount of a fungicidal composition comprising a compound of formula (I) to the fungus, soil, plant, root, foliage, seed or locus in which the infestation is to be prevented or to the growth medium of said fungus.

The compounds of the present invention have fungitoxic activity, particularly against phytopathogenic fungi. They are active against fungi of a number of classes including Deuteromycetes (Fungi Imperfecti), Basidiomycetes, Phycomycetes and Ascomycetes. More particularly, the method of this invention provides for activity against organisms including, but not limited to, *Pyricularia oryzae, Erysiphe graminis, Puccinia recondita, Colletotrichum lagenarium, Helminthosporium* species, *Altemaria solani, Septoria nodorum, Sclerotinia* species, *Sphaerotheca fuliginea, Plasmopara viticola, Pseudoperonospora cubensis, Cercospora* species, *Uncinula necator* and *Podosphaera leucotricha*. More particularly, rice diseases are controlled by the method of the invention. Examples of such rice diseases are seedborne diseases, soilborne diseases, and seedling box and field diseases such as those caused by *Pyricularia oryzae* and *Rhizoctonia* species. Additional diseases include powdery mildew incited by *Sphaerotheca fulignea* (e.g, cucurbit powdery mildew), *Uncinula necator* (e.g, grape powdery mildew), and *Podosphaera leucotricha* (e.g, apple powdery mildew). Cereal diseases are controlled such as those caused by *Erysiphe graminis, Puccinia recondita, Septoria nodurum* and *Helminthosporium* species. Tomato and potato diseases are controlled such as those caused by *Altemaria solani*.

The compounds are applied by any of a variety of known techniques, either as the compounds or as formulations comprising the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates.

Preferably, the compounds of the present invention are applied in the form of a formulation, comprising one or more of the compounds of Formula I with a phytologically acceptable carrier. Concentrated formulations can be dispersed in water, or other liquids, for application, or formulations can be dust-like or granular, which can then be applied without further treatment. The formulations can be prepared according to procedures that are conventional in the agricultural chemical art.

The present invention contemplates all vehicles by which one or more of the compounds can be formulated for delivery and use as a fungicide. Typically, formulations are applied as aqueous suspensions or emulsions. Such suspensions or emulsions are produced from water-soluble, water suspendable, or emulsifiable formulations which are solids, usually known as wettable powders; or liquids, usually known as emulsifiable concentrates, aqueous suspensions, or suspension concentrates. As will be readily appreciated, any material to which these compounds can be added may be used, provided they yield the desired utility without significant interference with the activity of these compounds as antifungal agents or damage to the plants or seeds.

Wettable powders, which may be compacted to form water dispersible granules, comprise an intimate mixture of one or more of the compounds of Formula I, an inert carrier and surfactants. The concentration of the compound in the wettable powder is usually from about 10 percent to about 90 percent by weight based on the total weight of the wettable powder, more preferably about 25 wt. percent to about 75 wt. percent. In the preparation of wettable powder formulations, the compounds can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I comprise a convenient concentration, such as from about 10 wt. percent to about 50 wt. percent of the compound, in a suitable liquid, based on the total weight of the concentrate. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulfated polyglycol ethers and appropriate salts of phosphated polyglycol ether.

Representative organic liquids which can be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Preferred organic liquids include xylene, and propyl benzene fractions, with xylene being most preferred. Surface-active dispersing agents are typically employed in liquid formulations and in an amount of from 0.1 to 20 percent by weight, based on the combined weight of the dispersing agent with one or more of the compounds. The formulations can also contain other compatible additives, for example, plant growth regulators and other biologically active compounds used in agriculture.

Aqueous suspensions comprise suspensions of one or more compounds of Formula I which have low water solubility, dispersed in an aqueous vehicle at a concentration in the range from about 5 to about 75 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The compounds of Formula I can also be applied as granular formulations, which are particularly useful for applications to the soil. Granular formulations usually contain from about 0.5 to about 10 wt. percent, bases on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I can be prepared by intimately mixing one or more of the compounds in powdered form with a suitable dusty agricultural carrier, such as, for example, kaolin clay, ground volcanic rock, and the like. Dusts can suitably contain from about 1 to about 10 wt. percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations that contain other pesticidal compounds. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I, and the pesticidal compound in the combination can generally be present in a weight ratio of from 1:100 to 100:1.

The compounds of Formula I can also be combined with other fungicides to form fungicidal mixtures and synergistic mixtures thereof. Fungicidal compounds are often applied in conjunction with one or more other fungicides to control a wider variety of undesirable diseases. When used in conjunction with other fungicide(s), the compounds of the present invention can be formulated with the other fungicide(s), tank mixed with the other fungicide(s) or applied sequentially with the other fungicide(s). Such other fungicides include enestrobin, antimycin, quinoxyfen, SYP-048, IK-1140, NC-224, 2-(thiocyanatomethylthio)-benzothiazole, 2-phenylphenol, 8-hydroxyquinoline sulfate, *Ampelomyces quisqualis*, azaconazole, azoxystrobin, *Bacillus subtilis*, benalaxyl, benomyl, benthiavalicarb-isopropyl, benzylaminobenzenesulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chinomethionate, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxinecopper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, piperalin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quintozene, Reynoutria sachalinensis extract, silthiofam, simeconazole, sodium 2-phenylphenoxide, sodium bicarbonate, sodium pentachlorophenoxide, spiroxamine, sulfur, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, tritiiconazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme: ampropylfos, anilazine, azithiram, barium polysulfide, Bayer 32394, benodanil, benquinox, bentaluron, benzamacril, benzamacril-isobutyl, benzamorf, binapacryl, bis(methylmercury)sulfate, bis(tributyltin)oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb, prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Additionally, the compounds of the present invention can be combined with other pesticides, including insecticides, nematocides, miticides, arthropodicides, bactericides or combinations thereof that are compatible with the compounds of the present invention in the medium selected for application, and not antagonistic to the activity of the compounds of the present invention to form pesticidal mixtures and synergistic mixtures thereof. Fungicidal compounds are often applied in conjunction with one or more other pesticides to control a wider variety of undesirable pests. When used in conjunction with other pesticides, triazine compounds can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoatemethyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cis-methrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spiromesifen; thiourea insecticides such as diafenthiuron; urea insecticides such as flucofuron and sulcofuron; and unclassified insecticides such as closantel, crotamiton, EXD, fenazaflor, fenoxacrim, flubendiamide, hydramethylnon, isoprothiolane, malonoben, metaflumizone, metoxadiazone, nifluridide, pyridaben, pyridalyl, rafoxanide, triarathene and triazamate, and any combinations thereof.

The compounds have broad ranges of efficacy as fungicides. The exact amount of the active material to be applied is dependent not only on the specific active material being applied, but also on the particular action desired, the fimgal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. The dilution and rate of application will depend upon the type of equipment employed, the method and frequency of application desired and diseases to be controlled, but the effective amount is usually from about 0.01 kilogram (kg) to about 20 kg, of active ingredient (a.i.) per hectare (ha). As a foliar fungicide, a compound of the present invention is usually applied to growing plants at a rate of about 0.1 to about 5 and preferably from about 0.125 to about 0.5 kg per hectare.

As a seed protectant, the amount of toxicant coated on the seed is usually at a dosage rate of about 10 to about 250 grams (g) and preferably from about 20 to about 60 g per 50 kilograms of seed. As a soil fungicide, the chemical can be incorporated in the soil or applied to the surface usually at a rate of 0.5 to about 20 kg and preferably about 1 to about 5 kg per hectare.

In particular, the compounds effectively control a variety of undesirable fungi that infect useful plant crops. Activity has been demonstrated for a variety of fungi, including those causing following the following plant diseases: Anthracnose of Cucumber (*Collatotrichum lagenarium*—COLLLA); Rice Blast (*Pyricularia oryzae*—PYRIOR); Late Blight of Tomato and Potato (*Phytophthora infestans*—PHYTIN); Leaf Rust of Wheat (*Puccinia recondite tritici*—PUCCRT); Powdery Mildew of Cucumber (*Erysiphe cichoracearum*—ERYSCI) and Glume Blotch of Wheat (*Septoria nodorum*—LEPTNO).

It will be understood by those in the art that the efficacy of the compound on the foregoing plant diseases establishes the general utility of the compounds as fungicides.

EXAMPLES

These examples are provided to further illustrate the invention. They are not meant to be construed as limiting the invention. Amounts are in weight parts or weight percentages unless otherwise indicated and temperatures are in degree Celcius unless otherwise indicated.

The compounds of the present invention have been prepared using the methods that are described below.

Scheme A

For compounds Compounds 1-35, and 58-76 using the appropriate reagents as defined below and having the appropriate $R^1$, $R^3$, $R^5$, X, Y and Y', which are well known in the art or commercially available.

Scheme A illustrates the method of preparation of an $R^3$—$R^5$—$N(R^1)$-4,5-dihydro-1,2,4-triazin-6(1H)-one

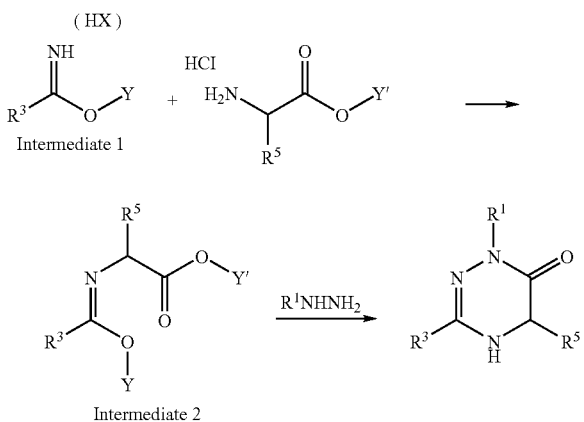

The imidic esters (Intermediate 1) can be formed by standard methods (for example, Neilson, D. G. in "The Chemistry of Amidines and Imidates", (S. Patai, ed.), Wiley Publishing Co., New York, N.Y. (1975) pp. 385-413 and references therein; Kiessling, A. J and McClure, C. K., Synthetic Communications 27(5), 923-927 (1997); and Schafer, F. C and Peters, G. A., J. Org. Chem. (1961) 26, 412). The $R^3$CN used to prepare the imidic esters (Intermediate 1) is commercially available or prepared by one skilled in the art for example methods shown in Scheme D. In the above equation, X is a counter ion such as chloride or bromide, Y is alkyl or aryl and Y' is aryl or arylalkyl. Preferably Y is alkyl and Y' is arylalkyl. The imidic esters may be neutral, or salts; wherein the case of salts, roughly one equivalent of base is added to the reaction. The reactions can be conducted in methylene chloride, dioxane with a small amount of ethanol, alcohol solvents such as ethanol, methanol or isopropanol, and is preferably conducted in methylene chloride with 5 percent ethanol. The reactions can be conducted at approximately 25° C. The product Intermediate 2 is reacted with a hydrazine to give the desired product. Solvents for this reaction include tetrahydrofuran, dioxane, or preferably an alcohol such as ethanol, propanol, etc.

Scheme B

Scheme B illustrates the method of preparation for Compounds 77-95 and specifically of an $R^3$—$N(R^1)$-1,2,4-triazin-6(1H)-one.

The dihydrotriazinones are oxidized to the triazinones by using 2,3-dichloro-5,6-dicyano-1,4-benzoquinone (DDQ) or ceric ammonium nitrate (CAN). The reaction is preferably run in ethyl acetate or ethyl acetate/THF mixture, although other solvents, such as aromatic hydrocarbons, can be used.

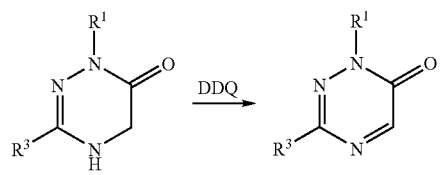

Scheme C

This illustrates the method of preparation of an $R^3$—N($R^1$)—$R^5$-4,5-dihydro-1,2,4-triazin-6(1H)-one for Compounds 36-57.

The 1,2,4-triazin-6-ones can react with nucleophiles such as alcohols or thiols to form 5-substituted derivatives.

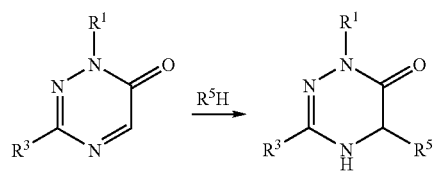

Scheme D

The nitrites, $R^3$CN, used to prepare the imidic esters (intermediate 1) of the present invention when not commercially available can be prepared by one skilled in the art according to for example the following methodologies, utilizing metal catalyzed coupling reactions widely known in the literature. Especially suitable are Pd(0) or Ni(0) catalyzed couplings which are well known to one skilled in the art as Stille coupling, Suziki couplings and Negishi couplings. A comprehensive review of these reactions can be found in Metal-Catalyzed Cross-Coupling Reactions; F. Diederich and P. Stang (eds.); Wiely-VCH; Weinheim 1998. Scheme D.1 and the following references describe preparation of $R^3$ as phenyl substituted for example by phenyl (n=0) in Tetrahedron (2001), 57(37), 7845-7855; phenylalkyl (n=1), phenylalkenyl in Journal of Organic Chemistry (2003), 68(20), 7733-7741. and phenylalkynyl in Journal of Organic Chemistry (1999), 64(24), 8873-8879. Typically a substituted boronic acid (or esters of boronic acids, preferably esters from 1,2 or 1,3-diols) is reacted with a substituted benzonitrile containing (R)n-L where L is preferably Cl, Br, I or a triflate. The coupling reaction is typically carried out in an acetonitrile/water mixture in the presence of a base such as sodium carbonate, potassium carbonate, sodium bicarbonate, cesium carbonate, triethylamine and a catalyst such as $(Ph_3)_4Pd$, $(Ph_3)_2PdCl_2$, pd(dba)$_2$, Pd(OAc)$_2$, dppbPdCl$_2$ and Pd(AOc)$_2$(o-tol)$_3$P.

Scheme D.1

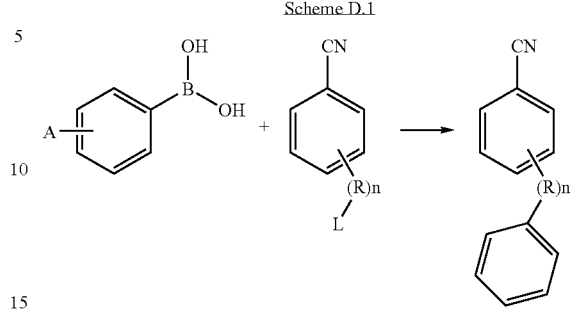

Scheme D.2

When $R^3$ is phenyl substituted by a heteroaryl a typical example is shown below

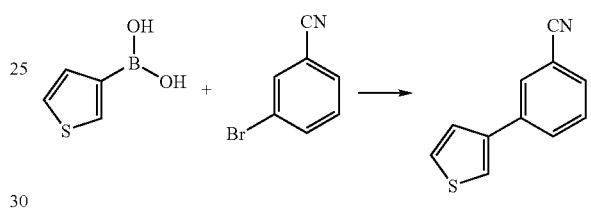

When $R^3$ is phenyl substituted by two heteroaryls or a heteroaryl and a halogen a typical example is shown below

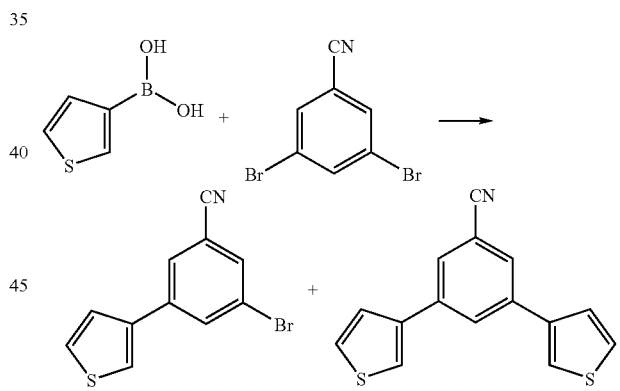

The mono and di-thienyl benzonitriles can be separated by conventional chromatographic techniques.

Scheme D.3

When $R^3$ is a substituted heteroaryl for example a substituted thienyl, substituted by for example by phenyl (n=0), phenylalkyl, phenylalkenyl and phenyl alkynyl (n=1). The $R^3$CN can be prepared as shown.

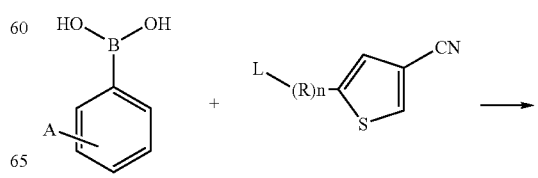

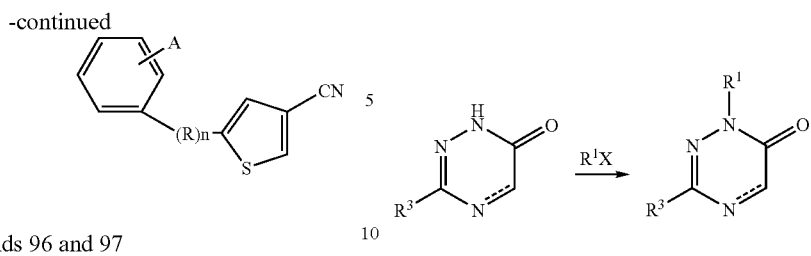

Scheme E for Compounds 96 and 97

Compounds can be alkylated at $N^1$ using a strong base such as sodium hydride or potassium t-butoxide in solvents such as DMF or THF. $R^1X$ is any alkylating agent.

The following procedures are representative synthesis examples of compounds of the present invention:

TABLE I

| Compound | Structure | Melting Point ° C./NMR/Mass Spec |
|---|---|---|
| 1 | 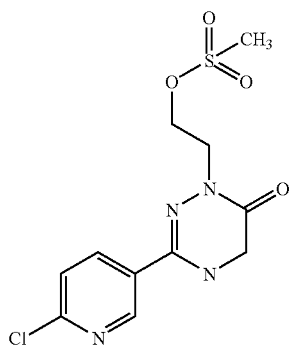 | (M + 1)(335.05, 333.14), (M − 1)(332.98, 331.04) |
| 2 | 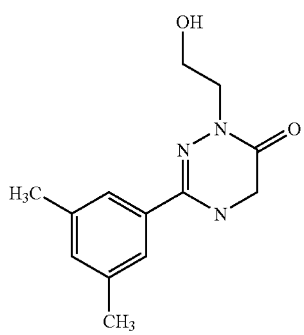 | (M + 1)248.22, (M − 1)245.86 |
| 3 | 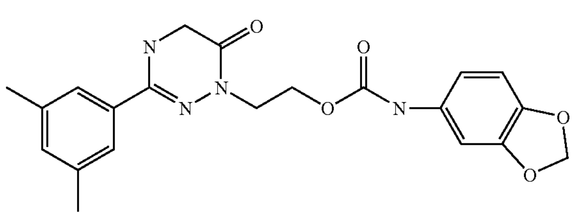 | (M + 1)410.92 (M − 1)408.92 |
| 4 | 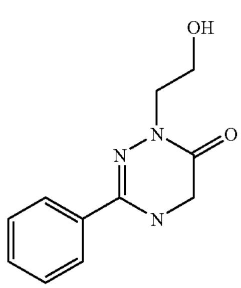 | 94-96° C. |

TABLE I-continued

| Compound | Structure | Melting Point ° C./NMR/Mass Spec |
|---|---|---|
| 5 | 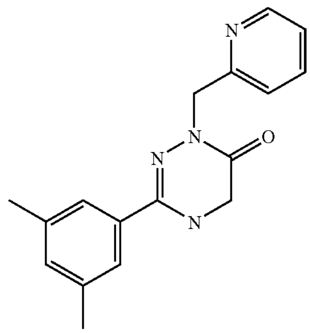 | 1H NMR (300 MHz, CDCl3): d 8.64(d, J=5.5 Hz, 1H), 7.76(t, J=7.4 Hz, 1H), 7.37(d, J=8.24 Hz, 1H), 7.24(m, 3H), 7.09(s, 1H), 5.23(s, 2H), 5.07(s, 1H), 4.22(s, 2H), 2.34(s, 6H). |
| 6 | 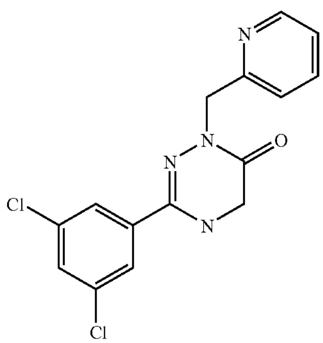 | 167-173° C. |
| 7 | 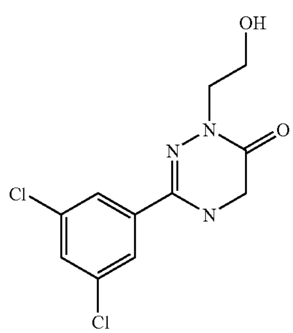 | 191-192° C. |
| 8 | 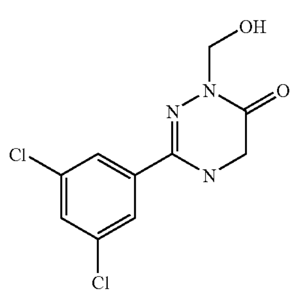 | 202-206° C. |
| 9 | 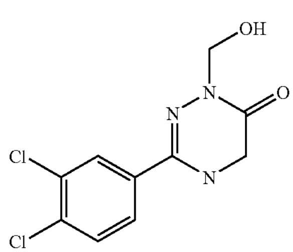 | 193-198° C. |

TABLE I-continued

| Compound | Structure | Melting Point ° C./NMR/Mass Spec |
|---|---|---|
| 10 | [3-(3,4-dichlorophenyl)-1-(trifluoroacetyl)-1,4-dihydro-1,2,4-triazin-6(5H)-one structure] | 203-204° C. |
| 11 | [3-(3,5-dichlorophenyl)-1-(trifluoroacetyl)-1,4-dihydro-1,2,4-triazin-6(5H)-one structure] | 154-157° C. |
| 12 | [3-(3,5-dimethylphenyl)-1-(trifluoroacetyl)-1,4-dihydro-1,2,4-triazin-6(5H)-one structure] | 1H NMR (300 MHz, CDCl3): 10.8(br s, 1H), 7.2 (br s, 3H), 5.5(s, 1H), 4.6(s, 2H), 2.4(s, 6H) |
| 13 | [3-(3,5-dichlorophenyl)-1-((diethoxymethoxy)methyl)-1,4-dihydro-1,2,4-triazin-6(5H)-one structure] | 1H NMR (300 MHz, CDCl3): 7.6(s, 2H), 7.4(s, 1H), 5.5(s, 1H), 5.4(s, 2H), 5.2(s, 1H), 4.1(s, 2H), 3.7-3.9(m, 4H), 1.3(m, 6H) |

TABLE I-continued
| Compound | Structure | Melting Point ° C./NMR/Mass Spec |
|---|---|---|
| 14 | 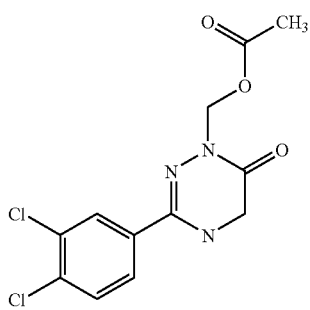 | 145-147° C. |
| 15 | 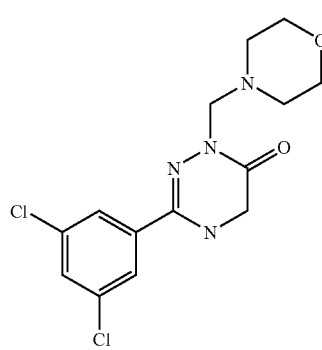 | 182-196° C. |
| 16 | 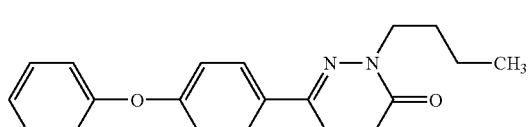 | $^1$HNMR (CDCl$_3$, 300 MHz) d/ppm 8.42(br, 2H), 7.66(dt, J$^1$=9.0 Hz, J$^2$=2.1 Hz, 2H), 7.35-7.30 (m, 2H), 7.04(dt, J$^1$=9.0 Hz, J$^2$=1.8 Hz, 2H), 4.99(br, 1H), 4.08(d, J=1.8 Hz, 2H), 3.78(t, J= 7.5 Hz, 2H), 1.72(pentet, J=7.8 Hz, 2H), 1.39 (sextet, J=7.5 Hz, 2H), 0.96(t, J=7.5 Hz, 3H). |
| 17 | 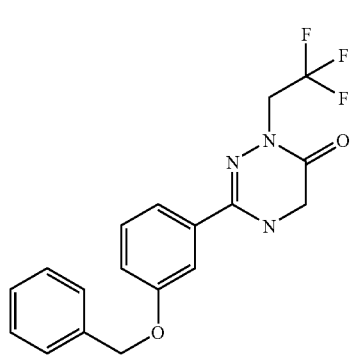 | (M + 1)364.06 (M − 1)361.90 |
| 18 | 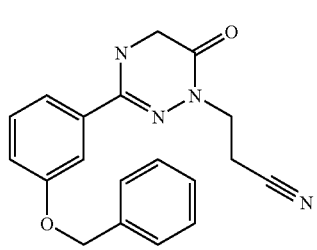 | (M + 1)335.05 (M − 1)332.98 |

TABLE I-continued

| Compound | Structure | Melting Point ° C./NMR/Mass Spec |
|---|---|---|
| 19 | 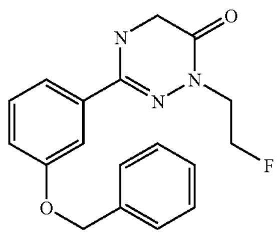 | (M + 1)328.21 (M − 1)325.94 |
| 20 | 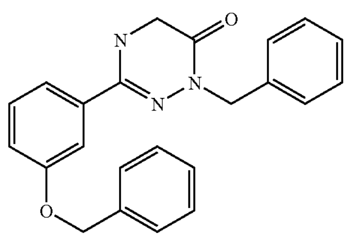 | (M + 1)372.10 (M − 1)369.94 |
| 21 | 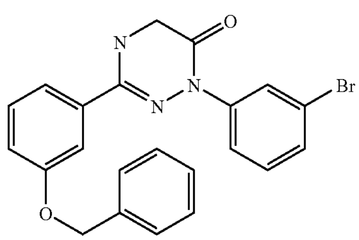 | (M + 1)(436.83, 435.70) (M − 1)(434.71, 433.61) |
| 22 | 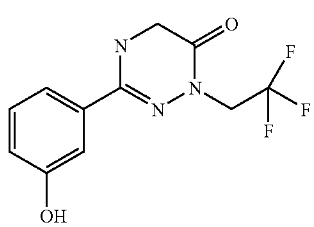 | (M + 1)274.10 (M − 1)271.84 |
| 23 | 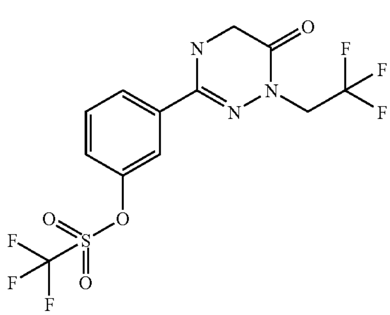 | (M + 1)405.64 (M − 1)403.63 |

TABLE I-continued

| Compound | Structure | Melting Point ° C./NMR/Mass Spec |
|---|---|---|
| 24 | 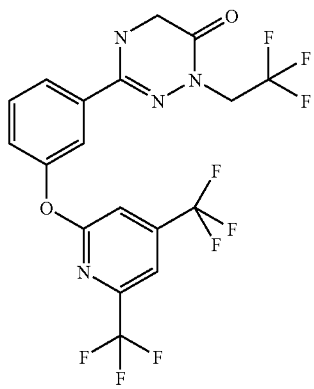 | (M + 1)486.73 (M − 1)484.71 |
| 25 | 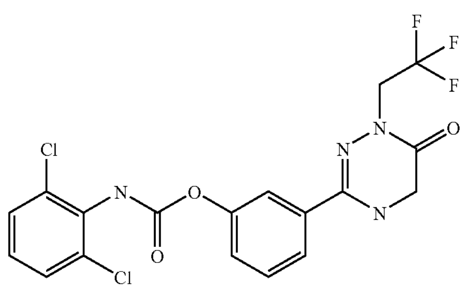 | (M + 1)(463.95, 460.98) |
| 26 | 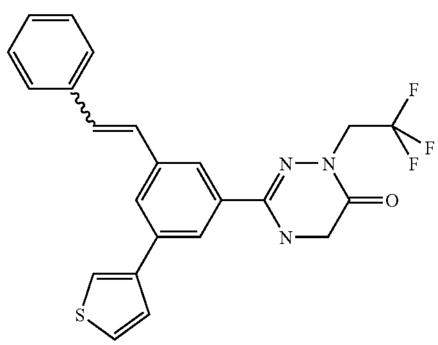 | 78-90° C. |
| 27 | 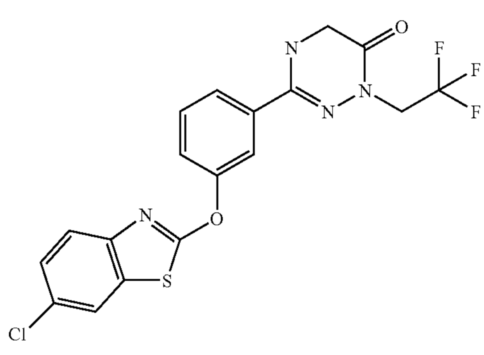 | (M + 1)(442.87, 440.93) (M − 1)(440.85, 438.91) |

TABLE I-continued

| Compound | Structure | Melting Point ° C./NMR/Mass Spec |
|---|---|---|
| 28 | 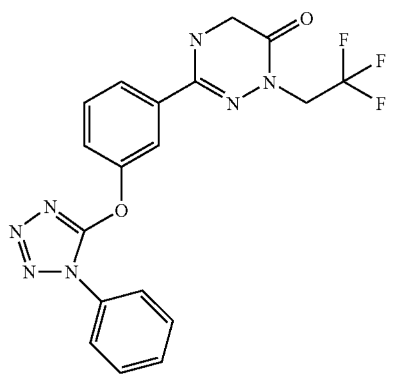 | (M + 1)417.74 (M − 1)415.71 |
| 29 | 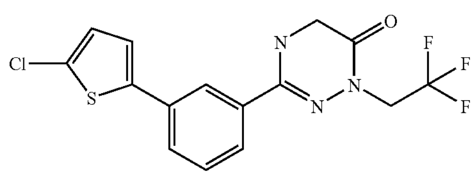 | (M + 1)(375.98, 374.21) (M − 1)(373.96, 372.19) |
| 30 | 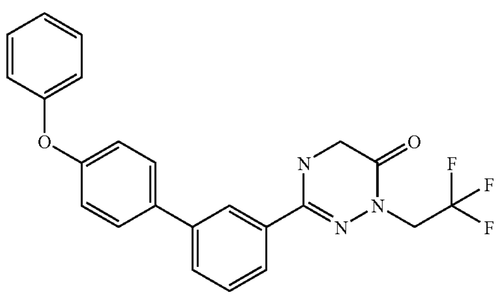 | (M + 1)425.87 (M − 1)423.75 |
| 31 | 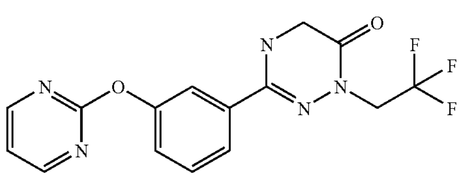 | (M + 1)352.54 (M − 1)350.06 |
| 32 | 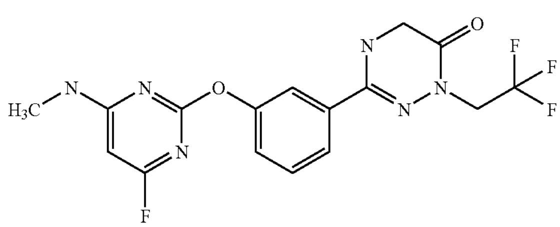 | (M + 1)398.85, (M − 1)396.84 |
| 33 | 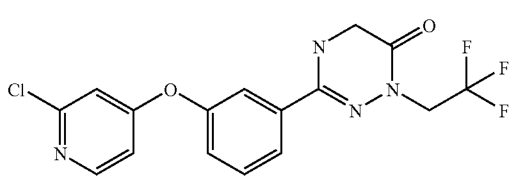 | (M + 1)(386.87, 385.16) (M − 1)(385.02, 383.01) |

TABLE I-continued

| Compound | Structure | Melting Point ° C./NMR/Mass Spec |
|---|---|---|
| 34 | 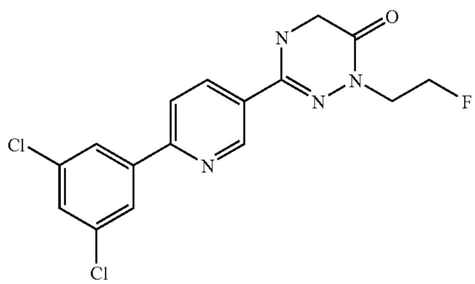 | (M + 1)(368.95, 367.66) (M − 1)(366.94, 365.65) |
| 35 | 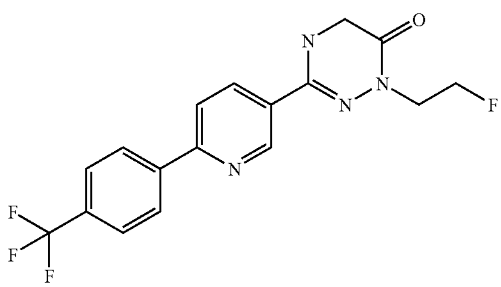 | (M + 1)393.07 (M − 1)391.06 |
| 36 | 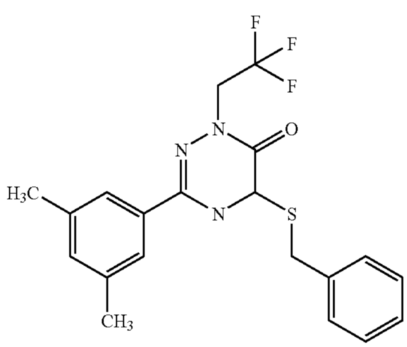 | 108-110° C. |
| 37 | 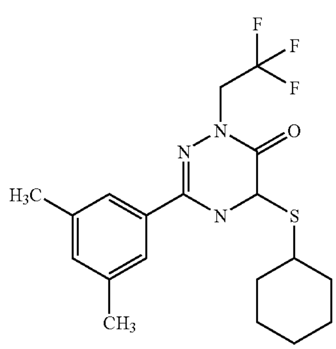 | 153.5-156.5° C. |

TABLE I-continued

| Compound | Structure | Melting Point ° C./NMR/Mass Spec |
|---|---|---|
| 38 | 3-(3,5-dimethylphenyl)-5-(2-hydroxyethylthio)-2-(2,2,2-trifluoroethyl)-2,5-dihydro-1,2,4-triazin-6(1H)-one | 114-117° C. |
| 39 | 5-(3-chloropropylthio)-3-(3,5-dimethylphenyl)-2-(2,2,2-trifluoroethyl)-2,5-dihydro-1,2,4-triazin-6(1H)-one | 149-152° C. |
| 40 | 5-(benzyloxy)-3-(3,5-dimethylphenyl)-2-(2,2,2-trifluoroethyl)-2,5-dihydro-1,2,4-triazin-6(1H)-one | 110, 160° C. |
| 41 | 5-(cyclohexyloxy)-3-(3,5-dimethylphenyl)-2-(2,2,2-trifluoroethyl)-2,5-dihydro-1,2,4-triazin-6(1H)-one | 138-141° C. |

TABLE I-continued

| Compound | Structure | Melting Point ° C./NMR/Mass Spec |
|---|---|---|
| 42 | 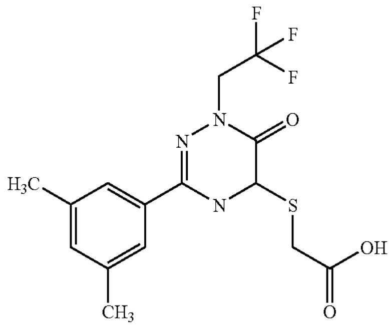 | 160-163° C. |
| 43 | 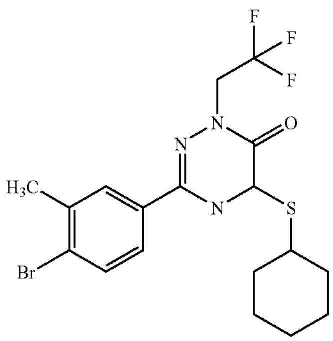 | 124-128° C. |
| 44 | 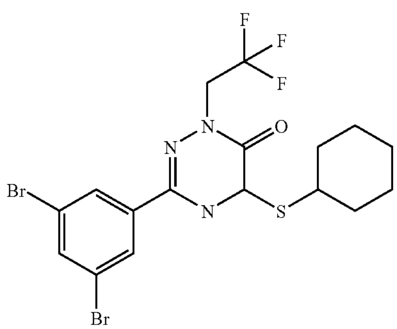 | 154-159° C. |
| 45 | 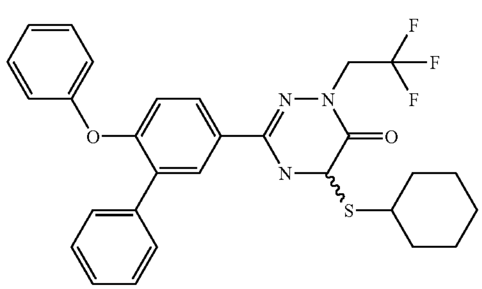 | 151-152° C. |
| 46 | 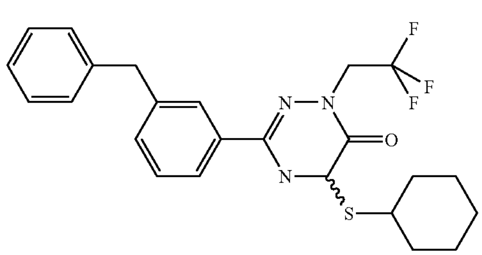 | 111-112° C. |

TABLE I-continued

| Compound | Structure | Melting Point ° C./NMR/Mass Spec |
|---|---|---|
| 47 | 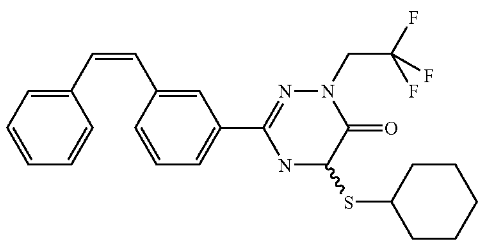 | 113-114° C. |
| 48 | 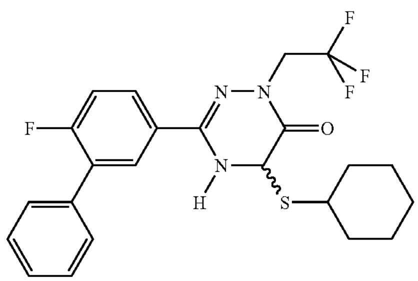 | 135-136° C. |
| 49 | 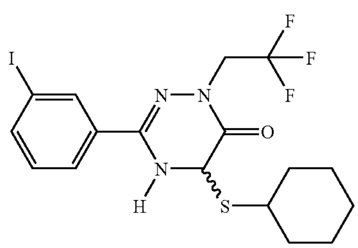 | 172-173° C. |
| 50 | 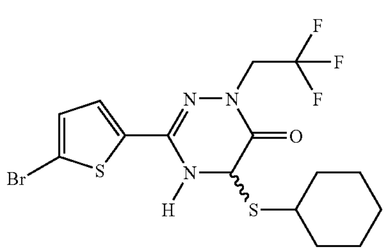 | 166-167° C. |
| 51 | 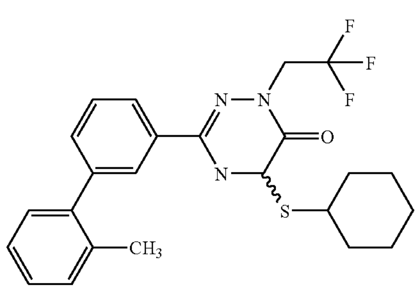 | 121-122° C. |

TABLE I-continued

| Compound | Structure | Melting Point °C./NMR/Mass Spec |
|---|---|---|
| 52 | 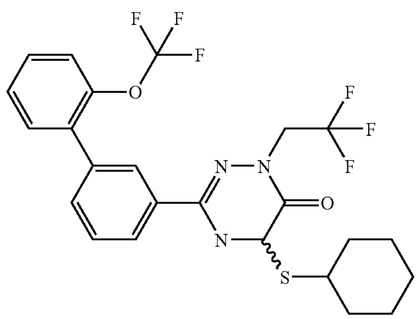 | 117-119° C. |
| 53 | 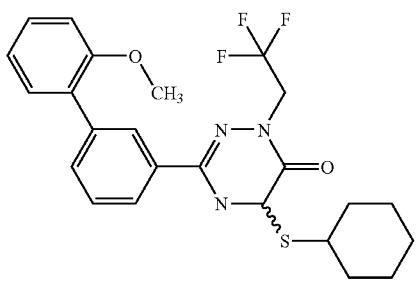 | 117-124° C. |
| 54 | 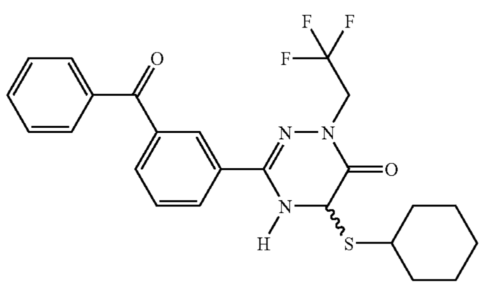 | 123-124° C. |
| 55 | 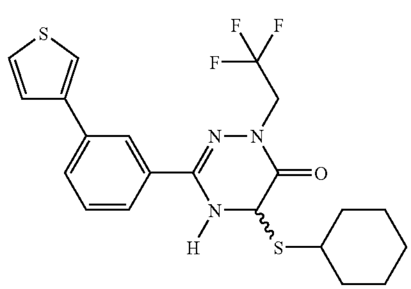 | 147-148° C. |
| 56 | 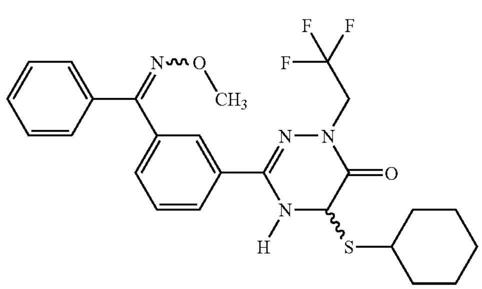 | 122-125° C. |

TABLE I-continued

| Compound | Structure | Melting Point ° C./NMR/Mass Spec |
|---|---|---|
| 57 | 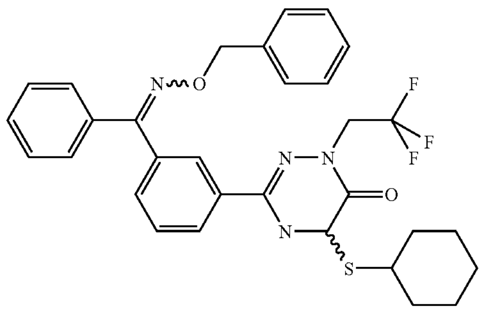 | 1HNMR (CDCl₃, 300 MHz) d/ppm 7.76-7.32 (m, 14H), 5.46(m, 0.5 H), 5.31(m, 0.5 H), 5.25-5.19(m, 3H), 4.61-4.48(m, 1H), 4.38-4.27(m, 1H), 3.08-2.97(m, 1H), 2.11-2.01(m, 1H), 1.98-1.87(m, 1H), 1.81-1.66(m, 2H), 1.63-1.53(m, 1H), 1.44-1.18(m, 5H). |
| 58 | 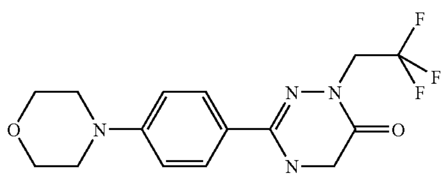 | 233-234° C. |
| 59 | 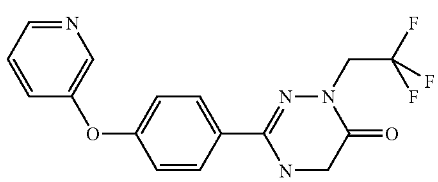 | 153-155° C. |
| 60 | 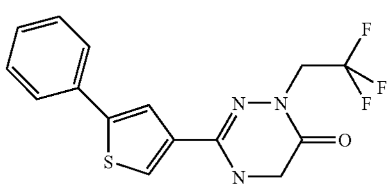 | 181-182° C. |
| 61 | 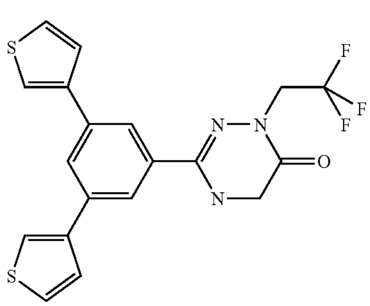 | 180-182° C. |

TABLE I-continued

| Compound | Structure | Melting Point ° C./NMR/Mass Spec |
|---|---|---|
| 62 | 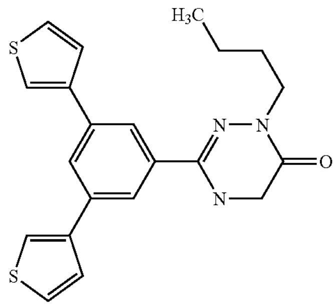 | 111-113° C. |
| 63 | 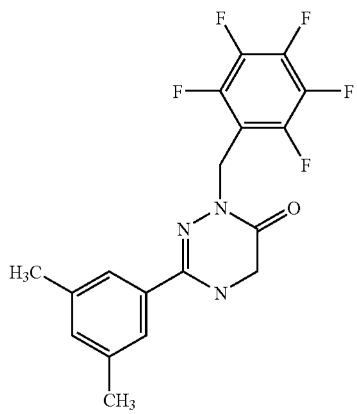 | 186-200° C. |
| 64 | 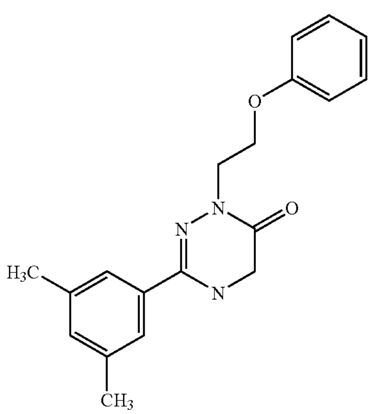 | 1H NMR (300 MHz, CDCl3): d 7.28(m, 4H), 7.10(s, 1H), 6.97(m, 3H), 5.02(s, 1H), 4.34(m, 2H), 4.22(m, 2H), 4.10(d, J=1.6 Hz, 2H), 2.36 (s, 6H). |
| 65 | 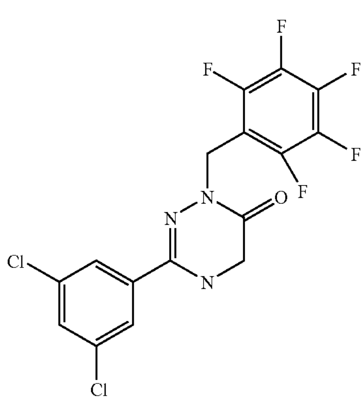 | 143-153° C. |

TABLE I-continued

| Compound | Structure | Melting Point ° C./NMR/Mass Spec |
|---|---|---|
| 66 | 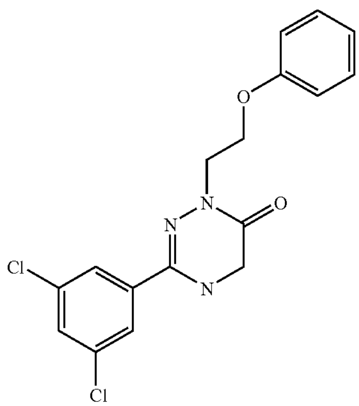 | 1H NMR (300 MHz, CDCl₃): d 7.54(m, 2H), 7.45(m, 1H), 7.29(m, 2H), 6.96(m, 3H), 4.99(s, 1H), 4.33(m, 2H), 4.21(m, 2H), 4.11(m, 2H). |
| 67 | 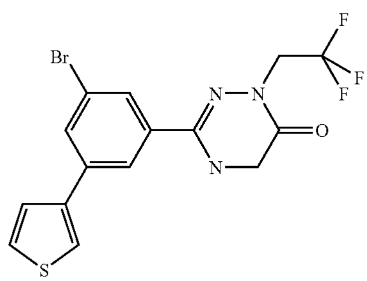 | 167-169° C. |
| 68 | 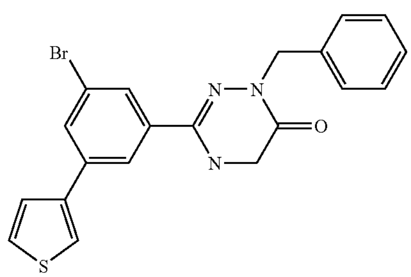 | 151-154° C. |
| 69 | 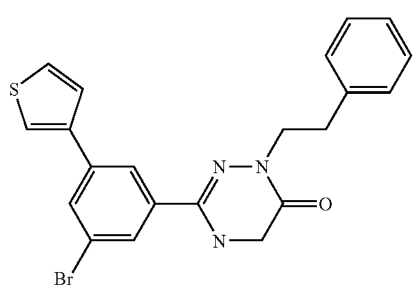 | 62-65° C. |
| 70 | 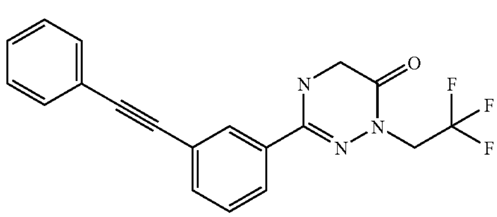 | (M + 1)358.02, (M − 1)355.86 |

TABLE I-continued

| Compound | Structure | Melting Point ° C./NMR/Mass Spec |
|---|---|---|
| 71 | 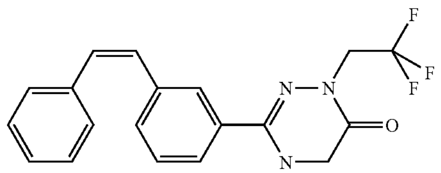 | 129-130° C. |
| 72 | 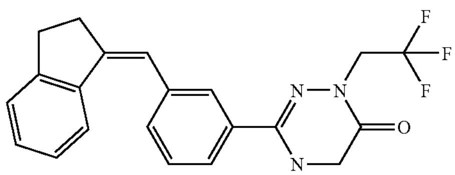 | 120-137° C. |
| 73 | 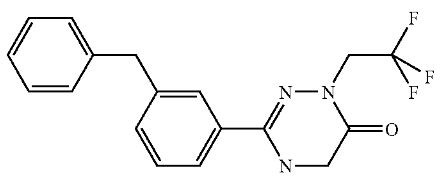 | 104-106° C. |
| 74 | 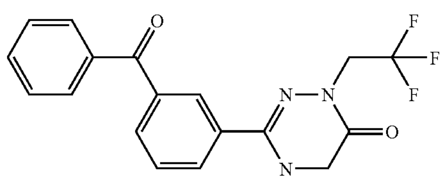 | 142-145° C. |
| 75 | 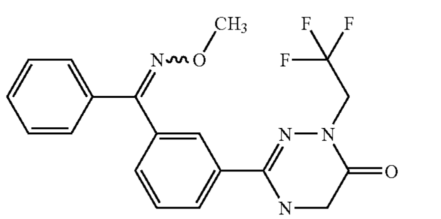 | 142-146° C. |
| 76 | 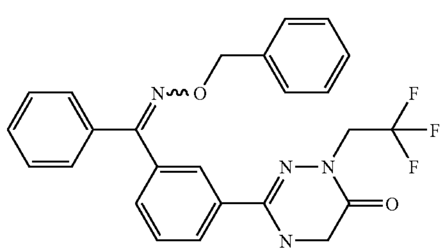 | 1HNMR (CDCl$_3$, 300 MHz) d/ppm 7.76-7.67 (m, 1.5H), 7.55-7.28(m, 12.5H), 5.25(s, 1H), 5.23(s, 1H), 5.03(br, 0.5H), 4.85(br, 0.5H), 4.39(q, J=8.7 Hz, 2H), 4.10(d, J=1.8 Hz, 1H), 4.05(d, J=1.8 Hz, 1H). |
| 77 | 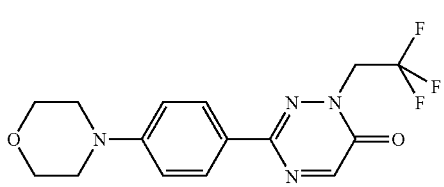 | 174-175° C. |
| 78 | 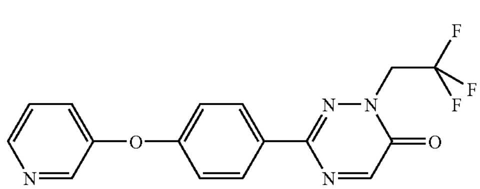 | 113-115° C. |

TABLE I-continued

| Compound | Structure | Melting Point ° C./NMR/Mass Spec |
|---|---|---|
| 79 | 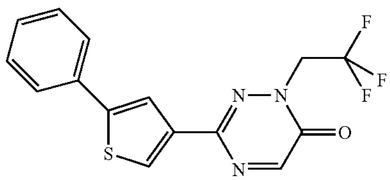 | 178-179° C. |
| 80 | 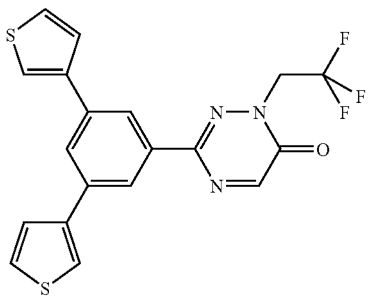 | 189-191° C. |
| 81 | 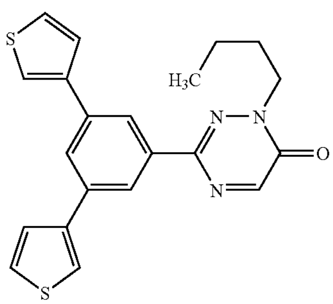 | 139-141° C. |
| 82 | 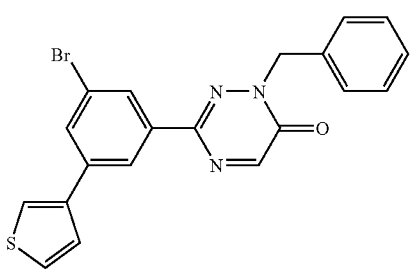 | 154-156° C. |
| 83 | 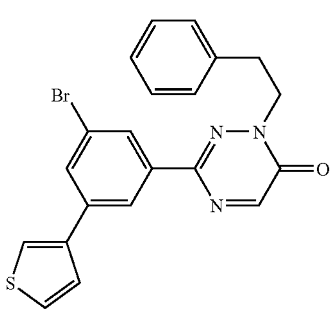 | 146-149° C. |

TABLE I-continued

| Compound | Structure | Melting Point ° C./NMR/Mass Spec |
|---|---|---|
| 84 | 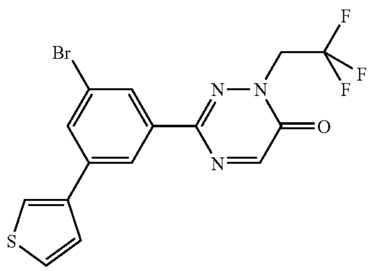 | 180-182° C. |
| 85 | 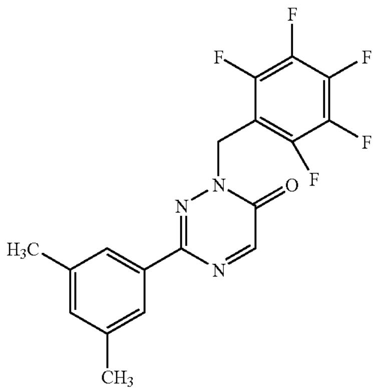 | 113-116° C. |
| 86 | 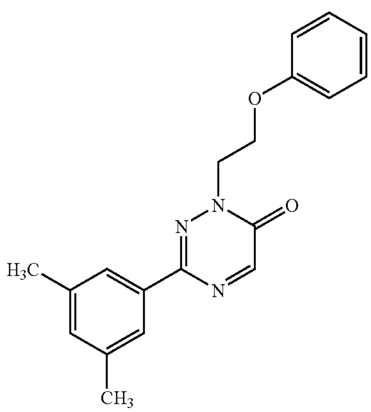 | 90-92° C. |
| 87 | 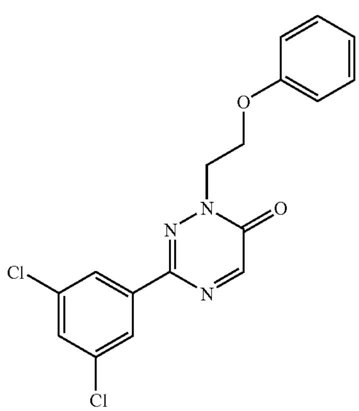 | 135-138° C. |

TABLE I-continued
| Compound | Structure | Melting Point ° C./NMR/Mass Spec |
|---|---|---|
| 88 | 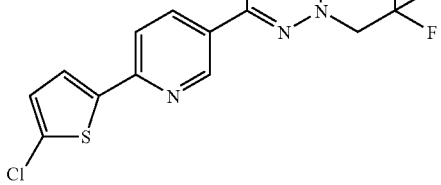 | (M + 1)(341.13, 339.39) (M − 1)(337.1, 339.27) |
| 89 | 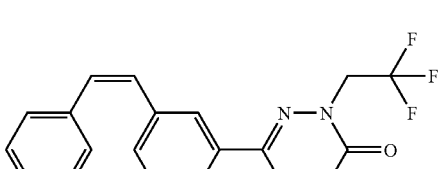 | 1HNMR (CDCl₃, 300 MHz) d/ppm 8.51(s, 1H), 8.03(br, 1H), 7.96(dt, J¹=6.9 Hz, 1H), 7.38-7.28(m, 2H), 7.26-7.19(m, 5H), 6.70(d, J= 12.3 Hz, 1H), 6.64(d, J=12.3 Hz, 1H), 4.71(q, J= 8.1 Hz, 2H). |
| 90 | 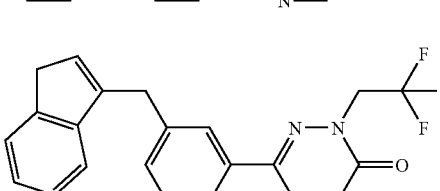 | 124-128° C. |
| 91 | 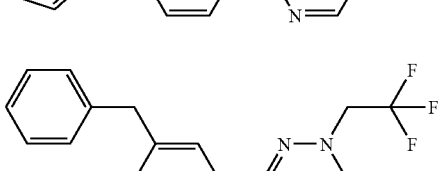 | 95-96° C. |
| 92 | 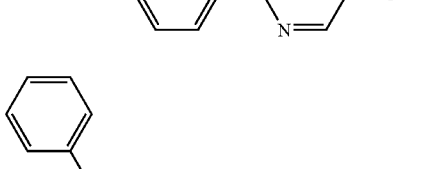 | 110-114° C. |
| 93 | 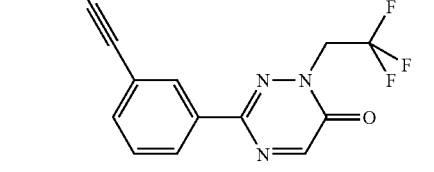 | 174-175° C. |
| 94 | 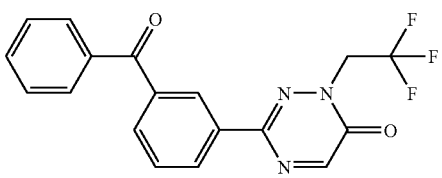 | 127-129° C. |

TABLE I-continued

| Compound | Structure | Melting Point ° C./NMR/Mass Spec |
|---|---|---|
| 95 | 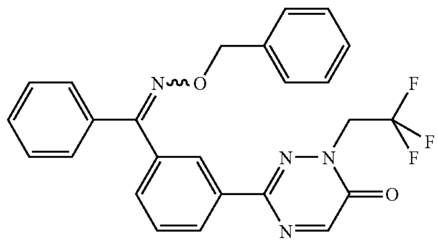 | 139-140° C. |
| 96 | 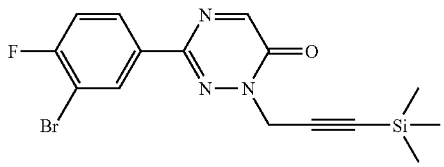 | 138-140° C. |
| 97 | 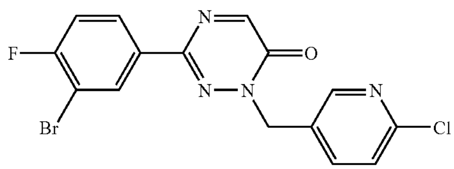 | 103-105° C. |

The following are representative Examples of the Compounds of the present invention.

Preparation of 3-(3,5-dithien-3-ylphenyl)-1-(2,2,2-trifluoroethyl)-4,5-dihydro-1,2,4-triazin-6(1H)-one (Compound 61)

Preparation of 3-Bromo-5-(thien-3-yl)benzonitrile and 3,5-(dithien-3-yl)benzonitrile A mixture of 3,5-dibromobenzonitrile (3 g, 11.5 mmol), thiophene-3-boronic acid (2.35 g, 18 mmol), dichlorobis(triphenylphosphine)palladium(II)(1.21 g, 1.7 mmol), tri-o-tolylphosphine (0.524 g, 1.7 mmol), sodium carbonate (3.46 g, 33 mmol) in aqueous acetonitrile (1:10), 110 mL) was refluxed under nitrogen for 6 hours, cooled to room temperature, concentrated under reduced pressure, suspended in hydrochloric acid (2N, 50 mL), and extracted with diethyl ether (3×80 mL). The combined organic extracts were washed with water (150 mL), saturated aqueous sodium bicarbonate (150 mL), and brine (50 mL), dried over magnesium sulfate, adsorbed onto silica, chromatographed on silica and eluted with a mobile phase of ethyl acetate in hexane. The first fraction was concentrated under reduced pressure to leave 3-bromo-5-(thien-3-yl)benzonitrile in the form of a yellow amorphous solid. Yield 1.47 g (48 percent). mp 62-63° C.; $^1$H NMR (CDCl$_3$) δ 7.94 (t, J=1.8 Hz, 1H), 7.79 (t, J=1.5 Hz, 1H), 7.69 (t, J=1.8 Hz, 1H), 7.54 (dd, J$^1$=3.0 Hz, J$^2$=1.5 Hz, 1H), 7.46 (dd, J$^1$=5.1 Hz, J$^2$=3.0 Hz, 1H), 7.34 (dd, J$^1$=4.8 Hz, J$^2$=1.5 Hz, 1H); EI/MS 265 m/e (M$^+$); IR (KBr) σ cm$^{-1}$ 2230.

The second fraction was concentrated under reduced pressure and recrystallised from ethyl acetate/hexane to afford 0.804 g (26 percent) of 3,5-(dithien-3-yl)benzonitrile as yellow needles. mp 122-124° C.; $^1$H NMR (CDCl$_3$) δ 7.99 (t, J=1.8 Hz, 1H), 7.77 (d, J=1.5 Hz, 2H), 7.56 (dd, J$^1$=2.7 Hz, J$^2$=1.5 Hz, 2H), 7.46 (dd, J$^1$=5.7 Hz, J$^2$=3.0 Hz, 2H), 7.40 (dd, J$^1$=5.1 Hz, J$^2$=1.5 Hz, 2H); EI/MS 267 m/e (M$^+$); CI/MS 268 m/e (M+1); IR (KBr) σ cm$^{-1}$ 2248.

Preparation of Ethyl 3,5-(dithien-3-ylphenyl)carboximidoate

This was made using the appropriate reaction materials via the procedure used in the synthesis of ethyl 3-benzylbenzenecarboximidoate (Compound 73). Yield of fluffy white solid 88 percent. mp 127-128° C.; $^1$H NMR (CDCl$_3$) δ 12.85 (br, 1H), 11.98 (br, 1H), 8.54 (s, 2H), 8.09 (s, 1H), 7.86 (s, 2H), 7.59 (d, J=4.2 Hz, 2H), 7.45 (s, 2H), 5.00 (br, 2H), 1.66 (br, 3H); ESI/MS 314 m/e (M+1).

Preparation of 3-(3,5-dithien-3-ylphenyl)-1-(2,2,2-trifluoroethyl)-4,5-dihydro-1,2,4-triazin-6(1H)-one This was prepared using the appropriate reaction materials via the procedure used in the synthesis of 3-(3-benzylphenyl)-1-(2,2,2-trifluoroethyl)-4,5-dihydro-1,2,4-triazin-6(1H)-one (Compound 73). Yield of amorphous yellow powder 57 percent. mp 180-182° C.; $^1$H NMR (CDCl$_3$) δ 7.88 (t, J=1.8 Hz, 1H), 7.76 (d, J=1.8 Hz, 2H), 7.54 (dd, J$^1$=2.7 Hz, J$^2$=1.8 Hz, 2H), 7.46-7.42 (m, 4H), 5.13 (br, 1H), 4.44 (q, J=8.7 Hz, 2H), 4.20 (d, J=1.2 Hz, 2H); ESI/MS 422 m/e (M+1); EI/MS 421 m/e (M$^+$).

Preparation of 3-(3-Bromo-5-thien-3-ylphenyl)-1-(2,2,2-trifluoroethyl)-4,5-dihydro-1,2,4-triazin-6(1H)-one (Compound 67)

This was prepared using the appropriate reaction materials via the procedure used in the synthesis of 3-(3-benzylphenyl)-1-(2,2,2-trifluoroethyl)-4,5-dihydro-1,2,4-triazin-6(1H)-one (Compound 73). Yield of orange solid 48 percent. mp 167-169° C.; $^1$H NMR (CDCl$_3$) δ 7.81 (t, J=1.5 Hz, 1H); 7.77 (t, J=3.0 Hz, 1H), 7.68 (t, J=1.8 Hz, 1H), 7.51 (ft, J$^1$=2.7

Hz, $J^2$=1.5 Hz, 1H), 7.43 (dd, $J^1$=5.1 Hz, $J^2$=3.0 Hz, 1H), 7.36 (dd, $J^1$=5.1 Hz, $J^2$=1.2 Hz, 2H), 5.10 (br, 1H), 4.42 (q, J=8.4 Hz; 2H), 4.17 (d, J=1.8 Hz, 2H); ES/MS 418 m/e (M$^+$); IR (KBr) σ cm$^{-1}$ 1675;.

Preparation of 3-(3-benzylphenyl)-1-(2,2,2-trifluoroethyl)-4,5-dihydro-1,2,4-triazin-6(1H)-one (Compound 73)

Preparation of 3-Benzylbenzonitrile

A mixture of benzeneboronic acid (2.05 g, 16.8 mmol), 3-bromomethylbenzonitrile (3 g, 15.3 mmol), dichlorobis(triphenylphosphine)palladium(II) (1.07 g, 1.53 mmol), tri-o-tolylphosphine (0.465 g, 29 mmol) and sodium carbonate (3.08 g, 29 mmol) in aqueous acetonitrile (1:10, 220 mL) was refluxed under nitrogen for 2 hours, cooled to room temperature, concentrated under reduced pressure, taken up in dilute hydrochloric acid (2N, 150 mL) and extracted with diethyl ether (3×70 mL). The organic extracts were combined, washed with water (2×100 mL), saturated aqueous sodium bicarbonate (100 mL), brine (70 mL), and dried over magnesium sulfate, then adsorbed on silica and chromatographed on silica using a mobile phase of ethyl acetate/hexane. The major fraction was concentrated under reduced pressure to leave a colorless liquid. Yield 2.1 g (71 percent). $^1$H NMR (CDCl$_3$) δ 7.49 (dt, $J^1$=7.5 Hz, $J^2$=1.2 Hz, 1H), 7.46 (br, 1H), 7.43 (dt, $J^1$=7.8 Hz, $J^2$=1.8 Hz, 1H), 7.39 (d, J=7.5 Hz, 1H), 7.33 (dt, $J^1$=6.9 Hz, $J^2$=2.1 Hz, 1H), 7.30 (dt, $J^1$=7.2 Hz, $J^2$=1.2 Hz, 1H), 7.25 (dt, $J^1$=7.2 Hz, $J^2$=1.5 Hz, 1H), 7.15 (dt, $J^1$=6.9 Hz, $J^2$=1.8 Hz, 2H), 4.01 (s, 2H); EI/MS 193 m/e (M$^+$); CI/MS 194 m/e (M+1);

Preparation of Ethyl 3-benzylbenzenecarboximidoate

Anhydrous hydrochloric acid was gently bubbled for 90 minutes into a solution containing 3-benzylbenzonitrile (1.0 g, 5.2 mmol) and absolute ethanol (0.45 mL, 7.8 mmol) in methylene chloride (7 mL) maintained at −4° C. After standing at 4° C. for a week, the reaction mixture was poured into 2:1 hexane/ether (500 mL), left at room temperature for 15 minutes and filtered. The residue was washed with 2:1 hexane/ether (50 mL) and dried in vacuo at room temperature. Yield 1.1 g (77 percent). mp 121-122° C.; $^1$H NMR (CDCl$_3$) δ 12.58 (br, 1H), 8.29-8.25 (m, 2H), 7.49-7.44 (m, 2H), 7.32-7.27(m, 2H), 7.22-7.18(m, 3H), 4.93 (q, J=6.9 Hz, 2H), 4.09 (s, 2H), 1.60 (t, J=6.9 Hz, 3H); EI/MS 240 m/e (M+1);

Preparation of 3-(3-benzylphenyl)-1-(2,2,2-trifluoroethyl)-4,5-dihydro-1,2,4-triazin-6(1H)-one A suspension of ethyl 3-benzylbenzenecarboximidoate (0.5 g, 1.8 mmol) in methylene chloride (100 mL) was washed with saturated aqueous sodium bicarbonate (2×80 mL) brine (50 mL), dried over magnesium sulfate and concentrated to 6 mL. To this was added benzylglycinate p-toluenesulfonate (0.615 g, 1.8 mmol) in portions over 10 minutes, stirred at room temperature under nitrogen for 14 hours, and concentrated under reduced pressure to leave a pink gum which was dissolved in absolute ethanol (6 mL). Following dropwise addition of a solution of 1,1,1-trifluoroethylhydrazine in ethanol (70 percent, 0.19 mL, 1.8 mmol), the reaction mixture was stirred at room temperature under nitrogen for 14 hours, adsorbed onto silica and chromatographed on silica, eluting with a ethyl acetate/hexane mobile phase. The major fraction was concentrated under reduced pressure to leave a fluffy, yellowish solid. Yield 0.345 g (63 percent). mp 104-106° C.; $^1$H NMR (CDCl$_3$) δ 7.50-7.46 (m, 2H), 7.37-7.16(m, 7H), 4.9 (br, 1H), 4.40 (q, J=8.7 Hz, 2H), 4.12 (s, 2H), 4.02 (s, 2H); ES/MS 347 m/e (M$^+$).

Preparation of 3-(Benzoyl)-1-(2,2,2-trifluoroethyl)-4,5-dihydro-1,2,4-triazin-6(1H)-one (Compound 74)

Preparation of 3-Benzoylbenzonitrile

This was prepared from the 3-benzylbenzonitrile according to the procedure of N A Noureldin, D Zhao and D. G. Lee in J. Org. Chem. (1997), 62, 8767-8772. A suspension of 3-benzylbenzonitrile (1.05 g, 5.4 mmol), potassium permanganate/copper(II)sulfate hexahydrate (1:1 mixture, 24.68 g) in methylene chloride (77 mL) was refluxed for 168 hours, cooled to room temperature, filtered through Celite, concentrated under reduced pressure to leave a waxy, white solid. Yield 1.1 g (98 percent). mp 84-85° C.; $^1$H NMR (CDCl$_3$) δ 8.07-8.03 (m, 2H), 7.87 (dt, $J^1$=7.5 Hz, $J^2$=1.2 Hz, 1H), 7.79-7.76 (m, 2H), 7.67-7.61 (m, 2H), 7.53 (t, J=7.5 Hz, 2H), 5.00 (br, 2H); EI/MS 207 m/e (M+1); ES/MS 208 m/e (M+1).

Preparation of Ethyl 3-benzoylcarboximidoate

This was made using the appropriate reaction materials via the procedure used in the synthesis of ethyl 3-benzylbenzenecarboximidoate (Compound 73). Yield 89 percent. mp 111-112° C.; $^1$H NMR (CDCl$_3$) δ 12.88 (br, 1H), 12.15 (br, 1H), 8.96 (ddd, $J^1$=7.8 Hz, $J^2$=2.1 Hz, $J^3$=0.9 Hz, 1H), 8.48 (t, J=1.5 Hz, 1H), 8.08 (ddd, $J^1$=6.6 Hz, $J^2$=$J^3$=1.2 Hz, 1H), 7.82-7.79 (m, 2H), 7.75 (t, J=7.5 Hz, 1H), 7.64 (tt, $J^3$=7.2 Hz, $J^2$=1.5 Hz, 1H), 7.54 (t, J=8.1 Hz, 2H), 7.51 (dt, $J^1$=6.9 Hz, $J^2$=0.9 Hz, 1H), 4.84 (q, J=6.9 Hz, 2H), 1.63 (t, J=6.9 Hz, 3H); EI/MS 254 m/e (M+1).

Preparation of 3-(Benzoyl)-1-(2,2,2-trifluoroethyl)-4,5-dihydro-1,2,4-triazin-6(1H)-one This was prepared via the procedure used in the synthesis of 3-(3-benzylphenyl)-1-(2,2,2-trifluoroethyl)-4,5-dihydro-1,2,4-triazin-6(1H)-one (Compound 73). Yield of amorphous yellow solid 57 percent. mp 142-145° C.; $^1$H NMR (CDCl$_3$) δ 8.05 (t, J=1.5 Hz, 1H), 7.97 (dt, $J^1$=7.8 Hz, $J^2$=1.8 Hz, 1H), 7.86 (dt, $J^1$=7.8 Hz, $J^2$=1.2 Hz, 1H), 7.81-7.78 (m, 2H), 7.63 (tt, $J^1$=7.5 Hz, $J^2$=1.5 Hz, 1H), 7.56 (t, J=7.5 Hz, 1H), 7.51 (t, J=7.5 Hz, 2H), 5.17 (br, 1H), 4.42 (q, J=8.7 Hz, 2H), 4.17 (d, J=1.8 Hz, 2H); ESI/MS 362 m/e (M+1).

Preparation of 3-{3-[(Z)-(Methoxyimino)phenyl)methyl]phenyl}-1-(2,2,2-trifluoroethyl)-4,5-dihydro-1,2,4-triazin-6(1H)-one (Compound 75)

This was prepared according to the method of A. Rosenthal in Can. J. Chem. (1960,)38, 2025-8. A solution of 3-(benzoyl)-1-(2,2,2-trifluoroethyl)-4,5-dihydro-1,2,4-triazin-6(1H)-one (0.3 g, 0.8 mmol) and O-methylhydroxylamine hydrochloride (0.111 g, 1.3 mmol) and pyridine (1 mL) in absolute ethanol (10 mL) was refluxed under nitrogen for 8 hours, cooled to room temperature, concentrated under reduced pressure, taken up in ethyl acetate (50 mL) washed with water (2×35 mL), brine (30 mL), dried over magnesium sulfate, adsorbed onto silica, chromatographed on silica using a mobile phase of ethyl acetate in hexane. The major fraction was concentrated under reduced pressure and dried in vacuo at room temperature for 14 hours to leave an amorphous yellow solid. Yield 0.31 g, 96 percent. mp 119-123° C.; $^1$H NMR (CDCl$_3$) δ 7.78-7.71 (m, 1H), 7.56-7.31 (m, 7H), 5.06-5.01(br, 1H), 4.40 (dq, J$^1$=8.7 Hz, J$^2$=2.4 Hz, 2H), 4.14 (d, J=1.5 Hz, 2H), 4.00 and 3.98 (both s, 1H total); ES/MS 391 m/e (M+1).

Preparation of 3-{3-[(Benzyloxyimino)phenyl)methyl]phenyl}-1-(2,2,2-trifluoroethyl)-4,5-dihydro-1,2,4-triazin-6(1H)-one (Compound 76)

The procedure used in the synthesis of 3-{3-[(Z)-(methoxyimino)phenyl)methyl]phenyl}-1-(2,2,2-trifluoroethyl)-4,5-dihydro-1,2,4-triazin-6(1H)-one (Compound 75) was used in this preparation using the appropriate reaction materials. Yield of yellow gum 98 percent. $^1$H NMR (CDCl$_3$) δ 7.76-7.67 (m, 1.5H), 7.55-7.28 (m, 12.5H), 5.25 (s, 1H), 5.23 (s, 1H), 5.03 (br, 0.5H), 4.85 (br, 0.5H), 4.39 (q, J=8.7 Hz, 2H), 4.10 (d, J=1.8 Hz, 2H), 4.05 (d, J=1.8 Hz, 1H); ESI/MS 467 m/e (M+1).

Preparation of 3-(3,5-dithien-3-ylphenyl)-1-(2,2,2-trifluoroethyl)-1,2,4-triazin-6(1H)-one (Compound 80)

This was prepared using the appropriate reaction materials via the procedure used in the synthesis of 3-(3-benzylphenyl)-1-(2,2,2-trifluoroethyl)-1,2,4-triazin-6(1H)-one (Compound 91). Yield of amorphous yellow solid 88 percent. mp 189-191° C.; $^1$H NMR (CDCl$_3$) δ 8.60 (s, 1H); 8.30 (d, J=1.2 Hz, 2H), 7.92 (t, J=1.8 Hz, 12H), 7.60 (ddt, J$^1$=2.7 Hz, J$^2$=1.5 Hz, 2H), 7.49 (dd, J$^1$=5.1 Hz, J$^2$=1.2 Hz, 2H), 7.45 (dd, J$^1$=4.8 Hz, J$^2$=2.7 Hz, 2H), 4.81 (q, J=7.8 Hz, 2H); ES/MS 418 m/e (M-1).

Preparation of 3-(3-Bromo-5-thien-3-ylphenyl)-1-(2,2,2-trifluoroethyl)-1,2,4-triazin-6(1H)-one (Compound 84)

This was prepared using the appropriate reaction materials via the procedure used in the synthesis of 3-(3-benzylphenyl)-1-(2,2,2-trifluoroethyl)-1,2,4-triazin-6(1H)-one (Compound 91). Yield of amorphous yellow solid 77 percent. mp 180-182° C.; $^1$H NMR (CDCl$_3$) δ 8.57 (s, 1H); 8.30 (t, J=1.8 Hz, 1H), 8.20 (t, J=1.8 Hz, 1H), 7.84 (t, J=1.5 Hz, 1H), 7.56 (dd, J$^1$=3.0 Hz, J$^2$=1.5 Hz, 1H), 7.45-7.40 (m, 2H), 4.79 (q, J=8.4 Hz, 2H); CI/MS 416 m/e (M$^+$); IR (KBr) σ cm$^{-1}$ 1677; Calculated for C$_{15}$H$_{11}$BrF$_3$N$_3$OS: C, 43.08; H, 2.65; N, 10.05. Found C, 42.94, H, 2.84; N, 9.22.

Preparation of 3-(3-Benzylphenyl)-1-(2,2,2-trifluoroethyl)-1,2,4-triazin-6(1H)-one (Compound 91)

A solution of 3-(3-benzylphenyl)-1-(2,2,2-trifluoroethyl)-4,5-dihydro-1,2,4-triazin-6(1H)-one (0.284 g, 0.8 mmol) and 2,3-dichloro-5,6-dicyano-1,4-quinone (DDQ, 0.204 g, 0.9 mmol) in ethyl acetate (9 mL) was refluxed for 5 hours, concentrated under reduced pressure, dissolved in methylene chloride (120 mL), washed with saturated aqueous sodium carbonate (2×60 mL), brine (70 mL), dried over magnesium sulfate and eluted through a silica gel plug. The filtrates were concentrated under reduced pressure to leave an amorphous yellow solid. Yield 0.267 g (95 percent). mp 95-96° C.; $^1$H NMR (CDCl$_3$) δ 8.54 (s, 1H), 8.00 (s, 1H), 7.98 (d, J=9.0 Hz, 1H), 7.39 (t, J=7.5 Hz, 1H), 7.32-7.28 (m, 3H), 7.23-7.20(m, 3H), 4.76 (q, J=7.8 Hz, 2H), 4.06 (s, 2H); ES/MS 346 m/e (M+1); IR (KBr) σ cm$^{-1}$ 1688.

Preparation of 3-(Benzoyl)-1-(2,2,2-trifluoroethyl)-1,2,4-triazin-6(1H)-one (Compound 93)

This was prepared using the appropriate reaction materials via the procedure used in the synthesis of 3-(3-benzylphenyl)-1-(2,2,2-trifluoroethyl)-1,2,4-triazin-6(1H)-one (Compound 91). Yield of amorphous white solid 93 percent. mp 174-175° C.; $^1$H NMR (CDCl$_3$) δ 8.58 (s, 1H), 8.57 (s, 1H), 8.37 (dt, J$^1$=8.1 Hz, J$^2$=1.2 Hz, 1H), 7.91 (dt, J$^1$=8.1 Hz, J$^2$=1.2 Hz, 1H), 7.84 (dd, J$^1$=8.1 Hz, J$^2$=1.2 Hz, 2H), 7.66-7.59 (m, 2H), 7.52 (t, J=7.8 Hz, 1H), 4.78 (q, J=8.4 Hz, 2H); ESI/MS 360 m/e (M+1).

Preparation of 3-{3-[(Z)-(Methoxyimino)phenyl)methyl]phenyl}-1-(2,2,2-trifluoroethyl)-1,2,4-triazin-6(1H)-one (Compound 94)

This preparation was based on the procedure used in the synthesis of 3-(3-benzylphenyl)-1-(2,2,2-trifluoroethyl)-1,2,4-triazin-6(1H)-one (Compound 91) using the appropriate reaction materials. Yield of yellow dried foam 89 percent. mp 127-129° C., $^1$H NMR (CDCl$_3$) δ 8.540 (s, 0.5H), 8.535 (s, 0.5H), 8.29 (t, J=1.8 Hz, 0.5H), 8.19 (dt, J$^1$=9.6 Hz, J$^2$=1.2 Hz,0.5H), 8.14-8.11 (m, 1.5H), 7.58-7.30 (m, 7H), 4.75 (dq, J$^1$=8.4 Hz, J$^2$=2.4 Hz, 2H), 4.01 (s, 1H), 3.99 (s, 1H); ESI/MS 389 m/e (M+1); IR (KBr) σ cm$^{-1}$ 2253, 1442, 1375.

Preparation of 3-{3-[(Benzyloxyimino)phenyl)methyl]phenyl}-1-(2,2,2-trifluoroethyl)-1,2,4-triazin-6(1H)-one (Compound 95)

This preparation was based on the procedure used in the synthesis of 3-(3-benzylphenyl)-1-(2,2,2-trifluoroethyl)-1,2,4-triazin-6(1H)-one (Compound 91) using the appropriate reaction materials. Yield of amorphous white solid 79 percent. mp 139-140° C., $^1$H NMR (CDCl$_3$) δ 8.54 (s, 0.5H), 8.53 (s, 0.5H), 8.26 (t, J=1.5 Hz, 0.5H), 8.20-8.16 (m, 1H), 8.11 (dt, J$^3$=7.2 Hz, J$^2$=1.8H, 0.5H), 7.56-7.27 (m, 12H), 5.27 (s, 1H), 5.25 (s, 1H), 4.74 (q, J=8.4 Hz, 2H); ES/MS 465 m/e (M+1).

Preparation of 5-cyclohexylthio-3-(3-iodophenyl)-1-(2,2,2-trifluoroethyl)-4,5-1,2,4-dihydrotriazin-6(1H)-one (Compound 49)

3-(3-iodophenyl)-1-(2,2,2-trifluoroethyl)-1,2,4-triazin-6(1H)-one, prepared according to procedure as taught in WO02/067675 (80 mg, 0.2 mmol) and mercaptocyclohexane (52 μL, 0.4 mmol) were combined in tetrahydrofuran (2 mL), stirred under nitrogen at room temperature for 5 days, concentrated under reduced pressure and titrated with an ether/hexane mixture to affect crystallization. Solids were thoroughly washed with ether/hexane, dried in vacuo at room temperature for 14 hours to leave an amorphous white solid in 92% yield. mp. 172-173° C. 1HNMR (CDCl$_3$, 300 MHz) δ/ppm 7.97 (t, J=1.8 Hz, 1H), 7.81 (ddd, J1=7.8 Hz, J2=1.8 Hz, J3=1.2 Hz, 1H), 7.18 (t, J=7.8 Hz, 1H), 5.40 (br, 1H), 5.23 (d, J=2.7 Hz, 1H), 4.60-4.50 (m, 1H), 4.39-4.26 (m 1H), 3.11-3.02 (m, 1H), 2.15-2.07 (m, 1H), 1.99-1.90 (m, 1H), 1.81-1.63 (m, 2H), 1.62-1.52 (m, 1H), 1.51-1.18 (m, 5H); ES/MS 498 m/e (M+1).

Preparation of 3-(3-bromo-4-fluorophenyl)-1-(3-trimethylsilanyl-prop-2-ynyl)-1,2,4-triazin-6(1H)-one (Compound 96)

To a stirred mixture of 3-(3-bromo-4-fluorophenyl)-1,2,4-triazin-6(1H)-one, prepared according to procedure as taught in WO02/067675 (50 mg), K$_2$CO$_3$ (179 mg, 1.3 mmol), and dimethylformamide (DMF) (5 mL) at 50° C. was added 3-trimethylsilylpropargyl bromide (35 mg) and the mixture was stirred until the disappearance of the starting material by Thin Layer Chromatography (TLC). When complete, the mixture was decanted into a separatory funnel with EtOAc (25 mL) and washed with dilute HCl (20 mL) and brine(20 mL), dried over sodium sulfate, filtered, and evaporated onto silica. The crude material was purified via flash column (20% then 40% Et$_2$O/Hex) and the product fractions were collected and evaporated to give 32 mg yellow solid, mp 103-105° C.

Preparation of (3-bromo-4-fluoro-phenyl)-1-(6-chloro-pyridin-3-ylmethyl)-1H-[1,2,4]triazin-6-one (Compound 97)

Step A

Preparation of 3-(3-bromo-4-fluorophenyl)-1-(6-chloropyridin-3-ylmethyl)-4,5-dihydro-1,2,4-triazin-6(1H)-one DMF was stirred for 10 min while being degassed with dry N2. 3-(3-bromo-4-fluorophenyl)-4,5-dihydro-1,2,4-triazin-6(1H)-one (200 mg 0.74 mmol) was then added and the mixture was degassed an additional 5 min. NaH (21 mg. 0.88 mmol) was added and the solution turned yellow; the solution was purged continuously with N$_2$, then 2-chloro-5-chloromethypyridine (143 mg. 0.88 mmol) was added. The flask was covered with aluminum foil and stirred at approximately 25° C. for approximately 48 hours. TLC indicated a mixture of the desired product and three other components. The reaction mixture was poured into 20 mL water and 30 mL EtOAc, extracted 2× with EtOAc and the combined organics were washed with brine, dried over MgSO4, filtered and evaporated. The crude residue was purified via flash column (50% EtOAc/Hex) and evaporation of the product fractions gave ~165 mg of material which (by NMR) appeared to be a mixture of the materials shown below.

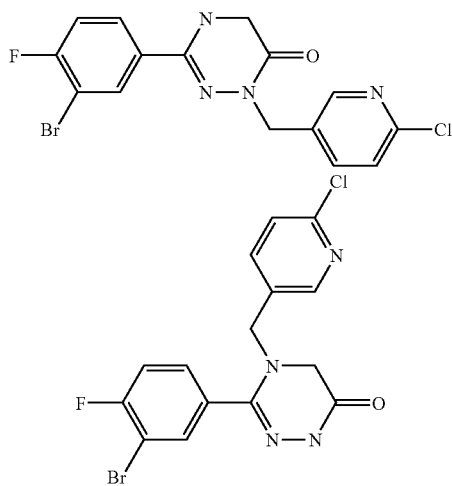

The mixture was then directly oxidized in Step B:

To a 100 mL round bottom flask was added tetrahydrofuran (THF) (5 mL) and EtOAc (5 mL) which was purged with N$_2$ for several minutes then the mixture from Step A (162 mg, 0.44 mmol) and ceric ammonium nitrate (CAN) (289 mg, 0.53 mmol) were added. The mixture was purged with N$_2$ continuously, TLC after 10 min indicated reaction was in progress. After 20 min, the reaction appeared complete. It was poured into EtOAc (25 mL) and washed with dilute HCl (20 mL) and the organic layer was separated, washed with brine (20 mL), dried over MgSO$_4$, filtered, and evaporated. The residue was purified via flash column (20% EtOAc/Hex) and evaporation of the product fractions gave ~60 mg of, 3-(3-bromo-4-fluoro-phenyl)-1-(6-chloro-pyridin-3-ylmethyl)-1H-[1,2,4]triazin-6-one, as a yellow solid, mp 138-140° C.

Biological Testing

The activity of the compounds as effective fungicides was determined by applying the compounds to plants and observing control and prevention of fungal disease. The technical compounds were formulated at 200 ppm in 10 volume percent acetone plus 90 volume percent Triton X water (deionized water 99.99 wt. percent+0.01 wt. percent Triton X100), giving a "formulated test compound." The compounds were tested for ability to control and prevent plant diseases on whole plants one to five days after application to leaves. Formulated test compounds were applied to plants using a turn table sprayer fitted with two opposing air atomization nozzles which delivered approximately 1500 L/ha of spray volume. Plants were inoculated with spores of the fungus one to five days later, then incubated in an environment conducive to disease development. Disease severity was evaluated 4 to 19 days after inoculation, depending on the speed of disease development.

Leaf Rust of Wheat (causal agent *Puccinia recondita tritici*=*Puccinia triticina*; Bayer code PUCCRT): Wheat plants (variety Yuma) were grown from seed in a soilless peat-based potting mixture (Metromix) until the seedlings were had a fully expanded first leaf. Each pot contained 3-8 seedlings. These plants were sprayed until wet with the formulated test compounds at a rate of 200 ppm. On the following day, the leaves were inoculated with an aqueous spore suspension of *Puccinia triticina* and the plants were kept in high humidity overnight to permit spores to germinate and infect the leaf. The plants were then transferred to a greenhouse until disease developed on untreated control plants.

Cucumber Anthracnose (causal agent Colletotricum lagenarium; Bayer code COLLLA): Cucumber plants (variety Bush Champion) were grown from seed in a soilless peat-based potting mixture (Metromix) until the first true leaf was 20-80 percent expanded. Each pot contained 1 seedling. These plants were sprayed until wet with the formulated test compound at a rate of 200 ppm. On the following day, the leaves were inoculated with an aqueous spore suspension of *Colletotricum lagenarium* and the plants were kept in high humidity for one day to permit spores to germinate and infect the leaf. The plants were then transferred to a growth chamber until disease developed on untreated control plants.

Cucumber Powdery Mildew (causal agent *Erysiphe cichoracaerum*; Bayer code ERYSCI): Cucumber plants (variety Bush Champion) were grown from seed in a soilless peat-based potting mixture (Metromix) until the first true leaf was 20-80 percent expanded. Each pot contained 1 seedling. These plants were sprayed until wet with the formulated test compound at a rate of 200 ppm. On the following day, the leaves were inoculated with an aqueous spore suspension of powdery mildew spores (approximately 50,000 spores per milliliter). The plants were then incubated in a greenhouse until disease developed on untreated control plants.

Glume Blotch of Wheat (causal agent *Leptosphaeria nodorum*=*Stagnospora nodorum*; Bayer code LEPTNO): Wheat plants (variety Yuma) were grown from seed in a 50 pasteurized soil/50 percent soil-less mix until the seedlings had a fully expanded first leaf. Each pot contained 3-20 seedlings. These plants were sprayed until wet with the formulated test compound at a rate of 200 ppm. On the following day, the leaves were inoculated with an aqueous spore suspension of *Leptosphaeria nodorum* and the plants were kept in high humidity (one day in a dark dew chamber followed by four to seven days in a lighted dew chamber) to permit spores to germinate and infect the leaf. The plants were then transferred to a greenhouse until disease developed on untreated control plants.

Tomato Late Blight (causal agent *Phytophthora infestans*; Bayer code PHYTIN): Tomato plants (variety Outdoor Girl or Rutgers) were grown from seed in a soilless peat-based potting mixture (Metromix) until the second true leaf was 30-100 percent expanded. Each pot contained 1 seedling. These plants were sprayed until wet with the formulated test compound at a rate of 200 ppm. On the following day, the leaves were inoculated with an aqueous suspension of *Phytophthora infestans* sporangia and zoospores, and the plants were kept in high humidity for one day to permit sporangia and zoospores to germinate and infect the leaf. The plants were then transferred to a growth chamber until disease developed on untreated control plants.

Rice Blast (causal agent *Magnaporthe grisea=Pyricularia oryzae*; Bayer code PYRIOR): Rice plants (variety M202) were grown from seed in a soilless peat-based potting mixture (Metromix) until the seedlings had a partly to fully expanded second leaf. Each pot contained 5-20 seedlings. These plants were sprayed until wet with the formulated test compound at a rate of 200 ppm. On the following day, the leaves were inoculated with an aqueous spore suspension of *Pyricularia oryzae* and the plants were kept in high humidity overnight to permit spores to germinate and infect the leaf. The plants were then transferred to a growth chamber at 22-24° C. until disease developed on untreated control plants.

TABLE II

Fungicidal activity of compounds on plant diseases in greenhouse tests.

| Compound | COLLLA | ERYSCI | LEPTNO | PHYTIN | PUCCRT | PYRIOR |
|---|---|---|---|---|---|---|
| 1 | + | + | + | + | + | ++ |
| 2 | + | + | + | + | + | +++ |
| 3 | ++ | + | ++ | + | +++ | +++ |
| 4 | + | + | + | + | + | + |
| 5 | ++ | + | +++ | + | + | + |
| 6 | ++ | + | +++ | + | +++ | +++ |
| 7 | + | + | ++ | + | ++ | + |
| 8 | + | + | ++ | + | + | + |
| 9 | + | + | +++ | + | ++ | + |
| 10 | ++ | + | ++ | + | + | +++ |
| 11 | ++ | + | ++ | + | + | ++ |
| 12 | NT | NT | NT | NT | NT | NT |
| 13 | NT | NT | NT | NT | NT | NT |
| 14 | + | + | + | + | ++ | + |
| 15 | + | + | ++ | + | + | +++ |
| 16 | + | + | + | + | +++ | + |
| 17 | +++ | + | +++ | + | +++ | +++ |
| 18 | ++ | + | ++ | + | +++ | ++ |
| 19 | + | + | ++ | + | +++ | ++ |
| 20 | + | + | ++ | + | +++ | +++ |
| 21 | + | + | ++ | + | ++ | +++ |
| 22 | + | + | + | + | ++ | + |
| 23 | + | + | ++ | + | ++ | +++ |
| 24 | + | + | +++ | + | +++ | + |
| 25 | + | + | + | + | + | + |
| 26 | + | + | ++ | + | + | + |
| 27 | ++ | + | +++ | + | +++ | +++ |
| 28 | + | + | ++ | + | + | ++ |
| 29 | + | + | +++ | + | +++ | ++ |
| 30 | + | + | ++ | + | ++ | + |
| 31 | + | + | ++ | + | + | + |
| 32 | + | + | +++ | + | ++ | + |
| 33 | + | + | ++ | + | +++ | + |
| 34 | ++ | + | +++ | ++ | +++ | +++ |
| 35 | ++ | + | +++ | ++ | +++ | +++ |
| 36 | +++ | + | +++ | + | +++ | +++ |
| 37 | +++ | + | +++ | + | +++ | +++ |
| 38 | + | + | +++ | + | +++ | +++ |
| 39 | +++ | + | +++ | + | +++ | +++ |
| 40 | +++ | + | +++ | + | +++ | +++ |
| 41 | ++ | + | +++ | + | +++ | +++ |
| 42 | +++ | + | +++ | + | +++ | +++ |
| 43 | +++ | + | +++ | +++ | +++ | +++ |
| 44 | +++ | + | +++ | +++ | +++ | +++ |
| 45 | ++ | + | +++ | + | ++ | +++ |
| 48 | +++ | + | +++ | + | +++ | +++ |
| 47 | +++ | +++ | +++ | + | +++ | +++ |
| 48 | ++ | + | +++ | ++ | +++ | +++ |
| 49 | +++ | + | +++ | + | +++ | +++ |
| 50 | ++ | + | +++ | + | +++ | +++ |
| 51 | ++ | + | +++ | + | +++ | +++ |

TABLE II-continued

Fungicidal activity of compounds on plant diseases in greenhouse tests.

| Compound | COLLLA | ERYSCI | LEPTNO | PHYTIN | PUCCRT | PYRIOR |
|---|---|---|---|---|---|---|
| 52 | + | + | +++ | + | +++ | +++ |
| 53 | ++ | + | +++ | + | +++ | +++ |
| 54 | ++ | + | +++ | + | ++ | +++ |
| 55 | ++ | + | +++ | + | ++ | +++ |
| 56 | + | + | +++ | + | ++ | +++ |
| 57 | + | + | + | + | + | + |
| 58 | + | ++ | + | + | + | +++ |
| 59 | + | ++ | ++ | ++ | +++ | ++ |
| 60 | + | + | +++ | + | + | +++ |
| 61 | + | + | + | + | +++ | +++ |
| 62 | + | + | +++ | + | + | + |
| 63 | + | + | ++ | + | + | ++ |
| 64 | ++ | + | +++ | + | +++ | +++ |
| 65 | +++ | + | +++ | + | + | ++ |
| 66 | +++ | + | +++ | + | +++ | +++ |
| 67 | +++ | + | +++ | + | +++ | +++ |
| 68 | + | + | +++ | + | + | +++ |
| 69 | + | + | ++ | + | + | ++ |
| 70 | + | + | + | + | + | +++ |
| 71 | + | + | +++ | + | ++ | ++ |
| 72 | + | + | +++ | + | +++ | +++ |
| 73 | + | + | +++ | + | +++ | +++ |
| 74 | ++ | + | +++ | + | +++ | ++ |
| 75 | + | + | +++ | + | +++ | +++ |
| 76 | + | + | ++ | + | ++ | +++ |
| 77 | +++ | ++ | ++ | ++ | + | +++ |
| 78 | +++ | + | ++ | +++ | +++ | +++ |
| 79 | ++ | + | +++ | + | +++ | +++ |
| 80 | + | + | + | + | ++ | +++ |
| 81 | + | + | +++ | + | + | + |
| 82 | + | + | +++ | + | + | ++ |
| 83 | + | + | ++ | + | + | + |
| 84 | ++ | + | +++ | + | + | +++ |
| 85 | +++ | + | +++ | + | +++ | +++ |
| 86 | +++ | + | +++ | + | +++ | +++ |
| 87 | + | + | + | + | + | + |
| 88 | + | + | ++ | + | + | + |
| 89 | ++ | + | +++ | + | +++ | +++ |
| 90 | + | + | ++ | + | ++ | +++ |
| 91 | +++ | +++ | +++ | + | +++ | +++ |
| 92 | +++ | + | ++ | ++ | +++ | +++ |
| 93 | + | + | +++ | + | ++ | +++ |
| 94 | + | + | +++ | + | +++ | +++ |
| 95 | + | + | ++ | + | + | +++ |
| 96 | ++ | + | + | + | ++ | +++ |
| 97 | ++ | + | +++ | + | +++ | +++ |

Ratings are based on percent control in a one-day protectant test at a 200 ppm application rate (+ = 0-49 percent control, ++ = 50-79 percent control, +++ = 80-100 percent control).

We claim:
1. A compound of the formula (I)

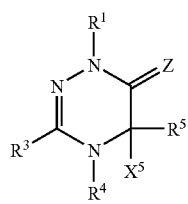

(I)

wherein
$R^1$ is selected from Group I or II; Group I consisting of:
alkyl, haloalkyl, cyanoalkyl, alkenyl, haloalkenyl, alkynyl, haloalkynyl, cycloalkylalkynyl, alkoxyalkyl, cycloalkyl, cycloalkylalkyl, trialkylsilylalkyl where the three alkyl groups may be the same or different, alkoxycarbonyl, alkylcarbonyl, alkoxycarbonylalkyl, phenyl optionally substituted with from one to three substituents independently selected from the group consisting of alkyl, halo, nitro, alkoxy, alkylthio, haloalkyl, haloalkylthio and haloalkoxy; phenalkyl optionally substituted on the phenyl ring with from one to three substituents independently selected from the group consisting of alkyl, halo, alkoxy, haloalkyl and haloalkoxy; pyridyl optionally substituted with from one to two substituents independently selected from the group consisting of alkyl and halo; furyl or thienyl, each optionally substituted with one to two substituents independently selected from halo and alkyl on the furyl or thienyl ring; and benzothienyl or benzofuranyl, each optionally substituted with one to two substituents independently selected from halo, alkyl and haloalkyl;

Group II consisting of:
a) aryloxyalkyl, haloalkoxyalkyl, haloalkoxyalkenyl, haloalkoxyalkynyl, trialkylsilylalkynyl where the three alkyl groups can be the same or different, substituted cycloalkylalkyl, cycloalkylalkenyl, cycloalkylcycloalkylalkyl, and cycloalkylalkylcycloalkylalkyl;
   wherein any cycloalkyl group above can be substituted with one to two substituents independently selected from the group consisting of alkylthio, haloalkyl, cyano, alkoxycarbonyl, alkoxycarbonylalkyl, alkoxycarbonylalkenyl, alkenoxycarbonyl, alkenoxycarbonylalkyl, alkenoxycarbonylalkenyl, alkylcarbonyl, alkylcarbonylalkyl, alkylcarbonylalkenyl, arylcarbonyl, arylcarbonylalkyl, arylcarbonylalkenyl, alkenylcarbonyl, alkenylcarbonylalkyl, alkenylcarbonylalkenyl, aryloxycarbonyl, aryloxycarbonylalkyl, aryloxycarbonylalkenyl, alkoxy, haloalkoxy, aryl, aralkyl, aralkenyl, heteroaryl, heteroarylalkyl, heteroarylalkenyl, heteroaryloxy, heteroaryloxyalkyl, and heteroaryloxyalkenyl,
      wherein any aryl or heteroaryl can be substituted with one to two substituents independently selected from the group consisting of alkyl, halo, alkoxy, haloalkyl, haloalkoxy, methylenedioxy and phenyl;
b) phenalkyl, optionally substituted on the phenyl ring with from four to five substituents independently selected from the group consisting of alkyl, halo, alkoxy, haloalkyl and haloalkoxy;
c) phenyl or phenalkyl, each substituted on the phenyl ring with one to two substituents independently selected from the group consisting of aryl, aryloxy, heteroaryl, heteroaryloxy, aralkyl, heteroarylalkyl, aryloxyalkyl and heteroaryloxyalkyl;
d) phenalkenyl, phenalkynyl, heteroarylalkyl, heteroarylalkenyl, and heteroarylalkynyl,
wherein alkyl, alkenyl, alkynyl can be substituted with halogen, alkoxy, or aryloxy; and
e) alkylcarbonyloxyalkyl, hydroxyalkyl, alkoxyalkyloxyalkyl, morpholinoalkyl, haloalkylcarbonyl, haloalkylcarbonylalkyl, alkenylcarbonylalkyl, haloalkenylcarbonylalkyl, alkynylcarbonylalkyl, haloalkynylcarbonylalkyl, arylcarbonylalkyl, aralkylcarbonylalkyl, aryloxyalkyl, alkylsulfonyloxyalkyl, heteroarylcarbonylalkyl, heteroarylalkylcarbonylalkyl, and arylaminocarbonyloxyalkyl;
   wherein any aryl or heteroaryl can be substituted with one to two substituents independently selected from the group consisting of alkyl, halo, alkoxy, haloalkyl, haloalkoxy, methylenedioxy and phenyl;
$R^3$ is selected from Group III or Group IV, Group III consisting of:
a) alkyl, cycloalkyl, cycloalkylalkyl or phenalkyl optionally substituted on the phenyl ring with from one to three substituents independently selected from the group consisting of alkyl, halo, alkoxy, haloalkyl and haloalkoxy;
b) phenyl optionally substituted with from one to five substituents independently selected from the group consisting of
   1) halo, alkyl, haloalkyl, haloalkoxy, alkylthio, haloalkylthio, alkylsulfinyl, alkylsulfonyl, nitro, cyano;
   2) phenyl or phenoxy, each optionally substituted with one or two substituents on the phenyl ring, independently selected from the group consisting of halo, alkyl, alkoxy, haloalkyl, haloalkoxy, alkylthio, nitro and cyano; and
   3) dialkylamino, wherein the alkyl groups may be the same or different or together with the nitrogen to which they are attached to form a 5- or 6-membered heterocyclic ring;
c) phenyl substituted solely with one heteroaryl group selected from the group consisting of:
   1) furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, and oxazol-5-yl;
      each optionally substituted with one or two substituents independently selected from halo, alkyl, alkoxy, haloalkoxy, haloalkyl, alkylthio, nitro and cyano; and
d) heteroaryl selected from pyrazinyl, pyrazolyl, 1,2,3-thiadiazol-4-yl, thiazolyl, triazolyl, triazinyl, isoxazolyl and oxazolyl;
   each optionally substituted with one or two substituents independently selected from halo, alkyl, alkoxy, haloalkoxy, haloalkyl, alkylthio, haloalkylthio, nitro and cyano;
and Group IV consisting of:
a) phenyl substituted with from one to three substituents independently selected from the group consisting of:
   hydroxyl, trihaloalkylsulfonyloxy, phenalkyl, phenalkenyl, phenalkynyl, indan-1-ylidenemethyl, phenalkoxy, phenylcarbonyl, phenalkenylcarbonyl, phencarbonylalkenyl, phen(alkoxyimino)methyl, phen(arylalkoxyimino)methyl, phencyclopropyl, phenylcyclopropylcarbonyl, phencarbonylcyclopropyl, phenaminocarbonyloxy, morpholinyl, heteroarylalkyl, heteroarylalkenyl, heteroarylcarbonyl, heteroaryloxy, where the heteroaryl ring and phenyl are substituted with from one to five substituents independently selected from the group consisting of:
   halo, alkyl, haloalkyl, haloalkoxy, alkylthio, haloalkylthio, alkylsulfinyl, alkylsulfonyl, nitro, phenyl, amino and cyano;
   and the phenyl ring of the indane can be further substituted with from one to five substituents independently selected from the group consisting of:
   halo, alkyl, haloalkyl, haloalkoxy, alkylthio, haloalkylthio, alkylsulfinyl, alkylsulfonyl, nitro and cyano;
b) phenyl substituted with at least two substituents independently selected from the groups consisting of:
   i) a heteroaryl selected from furyl, thienyl, benzothienyl, pyridyl, pyridazinyl, pyrimidinyl, pyrazinyl, and oxazol-5-yl, optionally substituted with one or two substituents independently selected from halo, alkyl, alkoxy, haloalkoxy, haloalkyl, alkylthio, nitro and cyano; and
   ii) halo, alkyl, phenalkenyl;
   wherein at least one of the substituents is selected from i);
c) heteroaryl selected from pyrimidinyl, pyrazinyl, 1,2,3-thiadiazol-4-yl and oxazolyl, each substituted with one or two substituents independently selected from phenyl, phenalkyl, phenalkenyl, phenalkynyl, heteroaryl, where the phenyl or heteroaryl ring is substituted with from one to five substituents independently selected from the group consisting of halo, alkyl, haloalkyl, haloalkoxy, alkylthio, haloalkylthio, alkylsulfinyl, alkylsulfonyl, nitro and cyano;
d) aryloxy, heteroaryloxy, aryloxyalkyl, heteroaryloxyalkyl; each optionally substituted on the aryl or heteroaryl ring with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring;
e) aryloxy, heteroaryloxy, aryloxyalkyl, heteroaryloxyalkyl substituted with a heteroaryl group selected from the group consisting of furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, and oxazol-5-yl;
each optionally substituted with one or two substituents independently selected from halo, alkyl, alkoxy, haloalkoxy, haloalkyl, alkylthio, nitro and cyano; and
f) arylcarbonyl, arylthio, arylamino, arylcarbonylalkyl, arylthioalkyl, arylaminoalkyl, heteroarylcarbonyl, heteroarylthio, heteroarylamino, heteroarylcarbonylalkyl, heteroarylthioalkyl, heteroarylaminoalkyl, arylcarbonyloxy, arylcarbonyloxyalkyl, arylcarbonylthio, arylcarbonylthioalkyl, arylcarbonylamino, arylcarbonylaminoalkyl;

$R^4$ is selected from the group consisting of:
a) alkylcarbonyl, alkylcarbonylalkyl, cycloalkylcarbonyl, alkylsulfonyl, alkylthio, amino, alkylamino, dialkylamino wherein the alkyl groups may be the same or different or together with the nitrogen to which they are attached form a 5- or 6-membered heterocyclic ring, cyano, alkenylsulfonyl, alkenylcarbonyl, alkoxycarbonyl, haloalkoxycarbonyl, alkoxycarbonylalkyl, alkoxycarbonylthio, (alkylthio)carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxycarbonyl; and
b) arylcarbonyl, arylsulfonyl, arylsulfonylalkenyl, aryloxycarbonyl, aryloxythiocarbonyl, arylthiothiocarbonyl; each substituted on the aromatic ring with one to two substituents independently selected from halo and alkyl;

$R^5$ is selected from the group consisting of:
a) a hydrogen atom, alkylcarbonyl, alkylcarbonylalkyl, formyl, alkoxy, alkoxycarbonyl, alkoxycarbonyloxy, alkylcarbonyloxy, alkylcarbonyloxyalkyl, alkoxycarbonylthio, alkylcarbonylthio, alkylthio, haloalkylthio, hydroxy, mercapto, carboxyalkylthio, hydroxyalkylthio, cycloalkyloxy, cycloalkylthio, carboxyalkylthio, cyano, amino; and
b) aryloxy, arylthio, aralkyloxy, aralkylthio or arylcarbonylthio;
each optionally substituted on the aryl ring with from one to three substituents independently selected from the group consisting of alkyl, halo, alkoxy, haloalkyl, haloalkoxy, amino, alkylamino and dialkylamino wherein the alkyl groups may be the same or different or together with the nitrogen to which they are attached form a 5- or 6-membered heterocyclic ring; or $R^4$ can form a fused ring to the $R^3$ substituent when the $R^3$ substituent is aryl or heteroaryl wherein $R^4$ is selected from —CH(R)—, —O—, —S—, —N(R)—, —C(=O)—, —O(C=O)—, —C(=O)O—, —CH$_2$CH$_2$—, —CH=CH—, —CH(R)O—, —OCH(R)—, —CH(R)S— and —SCH(R)—;
with the proviso that when $R^5$ is a hydrogen atom, alkylcarbonyl, alkylcarbonylalkyl, formyl, alkoxy, alkoxycarbonyl, alkoxycarbonyloxy, alkylcarbonyloxy, alkoxycarbonylthio, alkylcarbonylthio, alkylthio, hydroxy, mercapto, alkenyl, alkynyl, cyano, amino, aryloxy, arylthio, or arylcarbonylthio;

and
1) $R^1$ is selected from Group I, then $R^3$ is selected from Group IV, or
2) when $R^3$ is selected from Group III, then $R^1$ is selected from Group II;

$X^5$ is a hydrogen atom or taken together with $R^4$ forms a nitrogen-carbon bond,
Z is an oxygen atom, a sulfur atom or NR,
R is H or alkyl,
or an agronomically acceptable salt, isomer, tautomer, enantiomer or mixture thereof, provided that:
when $R^1$ is an aralkyl or a heteroarylalkyl, $R^4$ is not cyano, alkylsulfonyl, arylsulfonyl or polyhaloalkyl;
when $R^3$ is phenyl, $R^1$ is not benzyl or benzyloxymethyl;
when $R^1$ is hydroxyalkyl, $R^3$ is not chloropyridyl;
when $R^1$ is morpholinoalkyl, $R^3$ is not unsubstituted phenyl;
when $R^3$ is arylcarbonyl, $R^1$ is not phenyl or substituted phenyl; and
when $X^5$ is taken together with $R^4$ to form a nitrogen-carbon bond, $R^5$ is H.

2. The compound of claim 1 wherein $R^4$ is H and Z is O.
3. The compound of claim 2 wherein $R^5$ is selected from the group consisting of a hydrogen atom, alkylcarbonyl, haloalkylthio, hydroxyalkylthio, cycloalkyloxy, cycloalkylthio, carboxyalkylthio, aryloxy and arylthio.
4. The compound of claim 3 wherein $X^5$ is H.
5. The compound of claim 1 wherein $X^5$ taken together with $R^4$ forms a carbon-nitrogen bond and $R^5$ is hydrogen.
6. A fungicidal composition comprising a fungicidally effective amount of a compound of the formula:

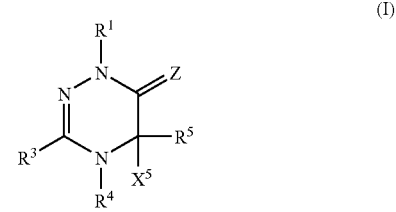

(I)

wherein
$R^1$ is selected from Group I or II; Group I consisting of:
alkyl, haloalkyl, cyanoalkyl, alkenyl, haloalkenyl, alkynyl, haloalkynyl, cycloalkylalkynyl, alkoxyalkyl, cycloalkyl, cycloalkylalkyl, trialkylsilylalkyl where the three alkyl groups may be the same or different, alkoxycarbonyl, alkylcarbonyl, alkoxycarbonylalkyl, phenyl optionally substituted with from one to three substituents independently selected from the group consisting of alkyl, halo, nitro, alkoxy, alkylthio, haloalkyl, haloalkylthio and haloalkoxy; phenalkyl optionally substituted on the phenyl ring with from one to three substituents independently selected from the group consisting of alkyl, halo, alkoxy, haloalkyl and haloalkoxy; pyridyl optionally substituted with from one to two substituents independently selected from the group consisting of alkyl and halo; furyl or thienyl, each optionally substituted with one to two substituents independently selected from halo and alkyl on the furyl or thienyl ring; and benzothienyl or benzofuranyl, each optionally substituted with one to two substituents independently selected from halo, alkyl and haloalkyl;

Group II consisting of:
a) aryloxyalkyl, haloalkoxyalkyl, haloalkoxyalkenyl, haloalkoxyalkynyl, trialkylsilylalkynyl where the three alkyl groups can be the same or different, substituted cycloalkylalkyl, cycloalkylalkenyl, cycloalkylcycloalkylalkyl, and cycloalkylalkylcycloalkylalkyl;
   wherein any cycloalkyl group above can be substituted with one to two substituents independently selected from the group consisting of alkylthio, haloalkyl, cyano, alkoxycarbonyl, alkoxycarbonylalkyl, alkoxycarbonylalkenyl, alkenoxycarbonyl, alkenoxycarbonylalkyl, alkenoxycarbonylalkenyl, alkylcarbonyl, alkylcarbonylalkyl, alkylcarbonylalkenyl, arylcarbonyl, arylcarbonylalkyl, arylcarbonylalkenyl, alkenylcarbonyl, alkenylcarbonylalkyl, alkenylcarbonylalkenyl, aryloxycarbonyl, aryloxycarbonylalkyl, aryloxycarbonylalkenyl, alkoxy, haloalkoxy, aryl, aralkyl, aralkenyl, heteroaryl, heteroarylalkyl, heteroarylalkenyl, heteroaryloxy, heteroaryloxyalkyl, and heteroaryloxyalkenyl,
      wherein any aryl or heteroaryl can be substituted with one to two substituents independently selected from the group consisting of alkyl, halo, alkoxy, haloalkyl, haloalkoxy, methylenedioxy and phenyl;
b) phenalkyl, optionally substituted on the phenyl ring with from four to five substituents independently selected from the group consisting of alkyl, halo, alkoxy, haloalkyl and haloalkoxy;
c) phenyl or phenalkyl, each substituted on the phenyl ring with one to two substituents independently selected from the group consisting of aryl, aryloxy, heteroaryl, heteroaryloxy, aralkyl, heteroarylalkyl, aryloxyalkyl and heteroaryloxyalkyl;
d) phenalkenyl, phenalkynyl, heteroarylalkyl, heteroarylalkenyl, and heteroarylalkynyl,
wherein alkyl, alkenyl, alkynyl can be substituted with halogen, alkoxy, or aryloxy; and
e) alkylcarbonyloxyalkyl, hydroxyalkyl, alkoxyalkyloxyalkyl, morpholinoalkyl, haloalkylcarbonyl, haloalkylcarbonylalkyl, alkenylcarbonylalkyl, haloalkenylcarbonylalkyl, alkynylcarbonylalkyl, haloalkynylcarbonylalkyl, arylcarbonylalkyl, aralkylcarbonylalkyl, aryloxyalkyl, alkylsulfonyloxyalkyl, heteroarylcarbonylalkyl, heteroarylalkylcarbonylalkyl, and arylaminocarbonyloxyalkyl;
   wherein any aryl or heteroaryl can be substituted with one to two substituents independently selected from the group consisting of alkyl, halo, alkoxy, haloalkyl, haloalkoxy, methylenedioxy and phenyl;

$R^3$ is selected from Group III or Group IV, Group III consisting of:
a) alkyl, cycloalkyl, cycloalkylalkyl or phenalkyl optionally substituted on the phenyl ring with from one to three substituents independently selected from the group consisting of alkyl, halo, alkoxy, haloalkyl and haloalkoxy;
b) phenyl optionally substituted with from one to five substituents independently selected from the group consisting of
   1) halo, alkyl, haloalkyl, haloalkoxy, alkylthio, haloalkylthio, alkylsulfinyl, alkylsulfonyl, nitro, cyano;
   2) phenyl or phenoxy, each optionally substituted with one or two substituents on the phenyl ring, independently selected from the group consisting of halo, alkyl, alkoxy, haloalkyl, haloalkoxy, alkylthio, nitro and cyano; and
   3) dialkylamino, wherein the alkyl groups may be the same or different or together with the nitrogen to which they are attached form a 5- or 6-membered heterocyclic ring;
c) phenyl substituted solely with one heteroaryl group selected from the group consisting of:
   1) furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, and oxazol-5-yl;
      each optionally substituted with one or two substituents independently selected from halo, alkyl, alkoxy, haloalkoxy, haloalkyl, alkylthio, nitro and cyano; and
d) heteroaryl selected from -pyridazinyl, pyrazinyl, pyrazolyl, 1,2,3-thiadiazol-4-yl, thiazolyl, triazolyl, triazinyl, isoxazolyl and oxazolyl;
   each optionally substituted with one or two substituents independently selected from halo, alkyl, alkoxy, haloalkoxy, haloalkyl, alkylthio, haloalkylthio, nitro and cyano;

and Group IV consisting of:
a) phenyl substituted with from one to three substituents independently selected from the group consisting of:
   hydroxyl, trihaloalkylsulfonyloxy, phenalkyl, phenalkenyl, phenalkynyl, indan-1-ylidenemethyl, phenalkoxy, phenylcarbonyl, phenalkenylcarbonyl, phencarbonylalkenyl, phen(alkoxyimino)methyl, phen(arylalkoxyimino)methyl, phencyclopropyl, phenylcyclopropylcarbonyl, phencarbonylcyclopropyl, phenaminocarbonyloxy, morpholinyl, heteroarylalkyl, heteroarylalkenyl, heteroarylcarbonyl, heteroaryloxy, where the heteroaryl ring and phenyl are substituted with from one to five substituents independently selected from the group consisting of:
      halo, alkyl, haloalkyl, haloalkoxy, alkylthio, haloalkylthio, alkylsulfinyl, alkylsulfonyl, nitro, phenyl, amino and cyano;
      and the phenyl ring of the indane can be further substituted with from one to five substituents independently selected from the group consisting of:
      halo, alkyl, haloalkyl, haloalkoxy, alkylthio, haloalkylthio, alkylsulfinyl, alkylsulfonyl, nitro and cyano;
b) phenyl substituted with at least two substituents independently selected from the groups consisting of:
   i) a heteroaryl selected from furyl, thienyl, benzothienyl, pyridyl, pyridazinyl, pyrimidinyl, pyrazinyl, and oxazol-5-yl, optionally substituted with one or two substituents independently selected from halo, alkyl, alkoxy, haloalkoxy, haloalkyl, alkylthio, nitro and cyano; and
   ii) halo, alkyl, phenalkenyl;
   wherein at least one of the substituents is selected from i);
c) heteroaryl selected from pyridazinyl, pyrazinyl, 1,2,3-thiadiazol-4-yl and oxazolyl, each substituted with one or two substituents independently selected from phenyl, phenalkyl, phenalkenyl, phenalkynyl, heteroaryl, where the phenyl or heteroaryl ring is substituted with from one to five substituents independently selected from the group consisting of halo, alkyl, haloalkyl, haloalkoxy, alkylthio, haloalkylthio, alkylsulfinyl, alkylsulfonyl, nitro and cyano;
d) aryloxy, heteroaryloxy, aryloxyalkyl, heteroaryloxyalkyl; each optionally substituted on the aryl or heteroaryl ring with from one to five substituents independently selected from the group consisting of halo, alkyl, haloalkyl, haloalkoxy, alkylthio, haloalkylthio, alkylsulfinyl, alkylsulfonyl, nitro, cyano, dialkylamino wherein the alkyl groups may be the same or different or together with the nitrogen to which they are attached form a 5- or 6-membered heterocyclic ring;

e) aryloxy, heteroaryloxy, aryloxyalkyl, heteroaryloxyalkyl substituted with a heteroaryl group selected from the group consisting of furyl, thienyl, quinolinyl, isoquinolinyl, benzofuranyl, benzothienyl, pyridyl, pyridazinyl, pyrimidinyl, pyrazinyl, 1,2,3-thiadiazol-4-yl, and oxazol-5-yl;

each optionally substituted with one or two substituents independently selected from halo, alkyl, alkoxy, haloalkoxy, haloalkyl, alkylthio, nitro and cyano; and f) arylcarbonyl, arylthio, arylamino, arylcarbonylalkyl, arylthioalkyl, arylaminoalkyl, heteroarylcarbonyl, heteroarylthio, heteroarylamino, heteroarylcarbonylalkyl, heteroarylthioalkyl, heteroarylaminoalkyl, arylcarbonyloxy, arylcarbonyloxyalkyl, arylcarbonylthio, arylcarbonylthioalkyl, arylcarbonylamino, arylcarbonylaminoalkyl;

$R^4$ is selected from the group consisting of:

a) alkylcarbonyl, alkylcarbonylalkyl, cycloalkylcarbonyl, alkylsulfonyl, alkylthio, amino, alkylamino, dialkylamino wherein the alkyl groups may be the same or different or together with the nitrogen to which they are attached form a 5- or 6-membered heterocyclic ring, cyano, alkenylsulfonyl, alkenylcarbonyl, alkoxycarbonyl, haloalkoxycarbonyl, alkoxycarbonylalkyl, alkoxycarbonylthio, (alkylthio)carbonyl, alkyl(thiocarbonyl), alkylthiothiocarbonyl, alkenyloxycarbonyl, alkenylthiothiocarbonyl, alkynyloxycarbonyl, alkynylthiothiocarbonyl, alkoxyoxalyl, alkylcarbonyloxyalkoxycarbonyl; and b) arylcarbonyl, arylsulfonyl, arylsulfonylalkenyl, aryloxycarbonyl, aryloxythiocarbonyl, arylthiothiocarbonyl; each substituted on the aromatic ring with one to two substituents independently selected from halo and alkyl;

$R^5$ is selected from the group consisting of:

c) a hydrogen atom, alkylcarbonyl, alkylcarbonylalkyl, formyl, alkoxy, alkoxycarbonyl, alkoxycarbonyloxy, alkylcarbonyloxy, alkylcarbonyloxyalkyl, alkoxycarbonylthio, alkylcarbonylthio, alkylthio, haloalkylthio, hydroxy, mercapto, carboxyalkylthio, hydroxyalkylthio, cycloalkyloxy, cycloalkylthio, carboxyalkylthio, cyano, amino; and d) aryloxy, arylthio, aralkyloxy, aralkylthio or arylcarbonylthio;

each optionally substituted on the aryl ring with from one to three substituents independently selected from the group consisting of alkyl, halo, alkoxy, haloalkyl, haloalkoxy, amino, alkylamino and dialkylamino wherein the alkyl groups may be the same or different or together with the nitrogen to which they are attached form a 5- or 6-membered heterocyclic ring; or $R^4$ can form a fused ring to the $R^3$ substituent when the $R^3$ substituent is aryl or heteroaryl wherein $R^4$ is selected from —CH(R)—, —O—, —S—, —N(R)—, —C(=O)—, —O(C=O)—, —C(=O)O—, —CH$_2$CH$_2$—, —CH=CH—, —CH(R)O—, —OCH(R)—, —CH(R)S— and —SCH(R)—;

with the proviso that when $R^5$ is a hydrogen atom, alkylcarbonyl, alkylcarbonylalkyl, formyl, alkoxy, alkoxycarbonyl, alkoxycarbonyloxy, alkylcarbonyloxy, alkoxycarbonylthio, alkylcarbonylthio, alkylthio, hydroxy, mercapto, alkenyl, alkynyl, cyano, amino, aryloxy, arylthio, or arylcarbonylthio; and 1) $R^1$ is selected from Group I, then $R^3$ is selected from Group IV, or 2) when $R^3$ is selected from Group III, then $R^1$ is selected from Group II;

$X^5$ is a hydrogen atom or taken together with $R^4$ forms a nitrogen-carbon bond, Z is an oxygen atom, a sulfur atom or NR, R is H or alkyl, or an agronomically acceptable salt, isomer, tautomer, enantiomer and mixture thereof, provided that:

when $R^1$ is an aralkyl or a heteroarylalkyl, $R^4$ is not cyano, alkylsulfonyl, arylsulfonyl or polyhaloalkyl;

when $R^3$ is phenyl, $R^1$ is not benzyl or benzyloxymethyl;

when $R^1$ is hydroxyalkyl, $R^3$ is not chloropyridyl;

when $R^1$ is morpholinoalkyl, $R^3$ is not unsubstituted phenyl;

when $R^3$ is arylcarbonyl, $R^1$ is not phenyl or substituted phenyl; and when $X^5$ is taken together with $R^4$ to form a nitrogen-carbon bond, $R^5$ is H.

7. The Compound of claim 5 wherein $R^4$ is H and Z is O.

8. The Compound of claim 6 wherein $R^5$ is selected from the group consisting of a hydrogen atom, alkylcarbonyl, haloalkylthio, hydroxyalkylthio, cycloalkyloxy, cycloalkylthio, carboxyalkylthio, aryloxy and arylthio.

9. The Compound of claim 7 wherein $X^5$ is H.

10. The compound of claim 1 wherein $X^5$ taken together with $R^4$ forms a carbon-nitrogen bond and $R^5$ is hydrogen.

11. A method of controlling a fungus comprising applying a fungicidally effective amount of a composition of claim 1 to the fungus, soil, plant, root, foliage, seed or locus in which the infestation is to be prevented or to the growth medium of said fungus.

* * * * *